United States Patent
Lücking et al.

(10) Patent No.: US 7,288,547 B2
(45) Date of Patent: Oct. 30, 2007

(54) CDK-INHIBITORY 2-HETEROARYL-PYRIMIDINES, THEIR PRODUCTION AND USE AS PHARMACEUTICAL AGENTS

(75) Inventors: Ulrich Lücking, Berlin (DE); Martin Kruger, Berlin (DE); Rolf Jautelat, Berlin (DE); Olaf Prien, Berlin (DE); Gerhard Siemeister, Berlin (DE); Alexander Ernst, Basel (CH)

(73) Assignee: Schering AG, Berlin (DE)

( * ) Notice: Subject to any disclaimer, the term of this patent is extended or adjusted under 35 U.S.C. 154(b) by 140 days.

(21) Appl. No.: 10/384,787

(22) Filed: Oct. 27, 2003

(65) Prior Publication Data

US 2004/0063737 A1    Apr. 1, 2004

Related U.S. Application Data

(60) Provisional application No. 60/430,053, filed on Dec. 2, 2002, provisional application No. 60/363,878, filed on Mar. 14, 2002.

(30) Foreign Application Priority Data

Mar. 11, 2002 (DE) ............... 102 12 100
Nov. 26, 2002 (DE) ............... 102 55 984

(51) Int. Cl.
- *C07D 401/12* (2006.01)
- *C07D 401/14* (2006.01)
- *C07D 403/12* (2006.01)
- *C07D 403/14* (2006.01)
- *A61K 31/433* (2006.01)
- *A61K 31/4196* (2006.01)
- *A61P 35/00* (2006.01)
- *C07D 409/12* (2006.01)
- *C07D 409/14* (2006.01)
- *C07D 417/12* (2006.01)
- *C07D 417/14* (2006.01)
- *A61K 31/4427* (2006.01)
- *A61K 31/381* (2006.01)

(52) U.S. Cl. ............ 514/272; 514/275; 544/320; 544/324; 544/325; 544/331

(58) Field of Classification Search ............ 544/320, 544/324, 325, 331; 514/275, 272
See application file for complete search history.

(56) References Cited

U.S. PATENT DOCUMENTS 6,197,779 B1 * 3/2001 Andries et al. ............ 514/272

FOREIGN PATENT DOCUMENTS

| WO | WO 99/02162 | 1/1999 |
|----|-------------|--------|
| WO | WO 0039101  | 7/2000 |
| WO | WO 01/14375 | 3/2001 |
| WO | WO 0164654  | 9/2001 |
| WO | WO 204429   | 1/2002 |

OTHER PUBLICATIONS

Cecil Textbook of Medicine, edited by Bennet, J.C., and Plum F., 20th edition, vol. 1, 1004-1010, 1996.*
Malumbres et al., Trends in Biochemical Sciences, 30(11), 630-641, 2005.*
Lolli et al., Cell Cycle 4 :4, 572-577, 2005.*
Sherr et al., Genes & Development 18, 2699-2711, 2004.*
Fischer Cell Cycle 3:6, 742-746, 2004.*

* cited by examiner

*Primary Examiner*—Venkataraman Balasubramanian
(74) *Attorney, Agent, or Firm*—Millen, White, Zelano & Branigan, P.C.

(57) ABSTRACT

This invention relates to 2-heteroaryl-pyrimidine derivatives of general formula I or I$_f$ as inhibitors of the cyclin-dependent kinases, their production as well as their use as medications for treating various diseases.

24 Claims, 1 Drawing Sheet

CDK-INHIBITORY 2-HETEROARYL-PYRIMIDINES, THEIR PRODUCTION AND USE AS PHARMACEUTICAL AGENTS

This application claims the benefit of the filing dates of U.S. Provisional Application Ser. No. 60/363,878 filed on Mar. 14, 2002 and U.S. Provisional Application No. 60/430,053, filed on Dec. 2, 2002.

This invention relates to 2-heteroaryl-pyrimidine derivatives, their production as well as their use as medications for treating various diseases.

The CDKs (cyclin-dependent kinase) is an enzyme family that plays an important role in the regulation of the cell cycle and thus is an especially advantageous target for the development of small inhibitory molecules. Selective inhibitors of the CDKs can be used for treatment of cancer or other diseases that cause disruptions of cell proliferation.

Pyrimidines and analogs are already described as active ingredients, such as, for example, the 2-anilino-pyrimidines as fungicides (DE 4029650) or substituted pyrimidine derivatives for treating neurological or neurodegenerative diseases (WO 99/19305). As CDK inhibitors, the most varied pyrimidine derivatives are described, for example bis(anilino)-pyrimidine derivatives (WO 00/12486), 2-amino-4-substituted pyrimidines (WO 01/14375), purines (WO 99/02162), 5-cyano-pyrimidines (WO 02/04429), anilinopyrimidines (WO 00/12486) and 2-hydroxy-3-N,N-dimethylaminopropoxy-pyrimidines (WO 00/39101).

The object of this invention is to provide compounds that have better properties than the inhibitors that are already known. The substances that are described here are more effective, since they already inhibit in the nanomolar range and can be distinguished from other already known CDK inhibitors such as, e.g., olomoucine and roscovitine.

It has now been found that compounds of general formula I

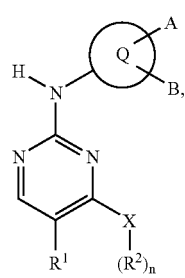

(I)

in which

Q stands for the group

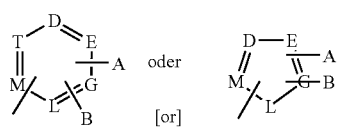

D, E, G,

L, M and T, in each case independently of one another, stand for carbon, oxygen, nitrogen or sulfur, whereby at least one heteroatom must be contained in the ring, $R^1$ stands for hydrogen, halogen, $C_1$-$C_6$-alkyl, $C_1$-$C_6$-alkinyl, nitro, cyano, heteroaryl or for the group —$COR^5$, —$OCF_3$, —S—$CF_3$ or —$SO_2CF_3$, $R^2$ stands for hydrogen, $C_1$-$C_{10}$-alkyl, $C_2$-$C_{10}$-alkenyl, $C_2$-$C_{10}$-alkinyl, aryl, heteroaryl or $C_3$-$C_7$-cycloalkyl or for $C_1$-$C_{10}$-alkyl, $C_2$-$C_{10}$-alkenyl, $C_2$-$C_{10}$-alkinyl, aryl, heteroaryl or $C_3$-$C_7$-cycloalkyl that is optionally substituted in one or more places in the same way or differently with hydroxy, halogen, $C_1$-$C_6$-alkoxy, $C_1$-$C_6$-alkylthio, amino, cyano, $C_1$-$C_6$-alkyl, $C_2$-$C_6$-alkenyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_3$-$C_7$-cycloalkyl, —$NHC_1$-$C_6$-alkyl, —$NHC_3$-$C_7$-cycloalkyl, —$N(C_1$-$C_6$-alkyl$)_2$, —$SO(C_1$-$C_6$-alkyl), —$SO_2$ ($C_1$-$C_6$-alkyl), $C_1$-$C_6$-alkanoyl, —$CONR^3R^4$, —$COR^5$, $C_1$-$C_6$-alkylOAc, phenyl or with the group $R^6$, the ring of the $C_3$-$C_7$-cycloalkyl optionally can be interrupted by one or more nitrogen, oxygen and/or sulfur atoms and/or can be interrupted by one or more =C=O groups in the ring and/or optionally one or more possible double bonds can be contained in the ring, and the phenyl, aryl or $C_3$-$C_7$-cycloalkyl itself optionally can be substituted in one or more places in the same way or differently with halogen, hydroxy, $C_1$-$C_6$-alkyl, or $C_1$-$C_6$-alkoxy, or with the group —$CF_3$ or —$OCF_3$, X stands for halogen, oxygen, sulfur or for the group —NH— or —N($C_1$-$C_3$-alkyl)-, or X and $R^2$ together form a $C_3$-$C_{10}$-cycloalkyl ring, which optionally can contain one or more heteroatoms and optionally can be substituted in one or more places with hydroxy, $C_1$-$C_6$-alkyl, hydroxy-$C_1$-$C_6$-alkyl or halogen, A and B, in each case independently of one another, stand for hydrogen, hydroxy, halogen, or for the group —$SR^7$, —$S(O)R^7$, —$SO_2$ $R^7$, —$NHSO_2$ $R^7$, —CH(OH)$R^7$, —$CR^7$ (OH)—$R^7$, $C_1$-$C_6$-alkylP(O)$OR^3OR^4$ or —$COR^7$, or A and B together form a $C_3$-$C_7$-cycloalkyl ring that optionally can be interrupted by one or more nitrogen, oxygen and/or sulfur atoms and/or can be interrupted by one or more =C=O groups in the ring and/or optionally one or more possible double bonds can be contained in the ring, and the $C_3$-$C_7$-cycloalkyl ring optionally can be substituted in one or more places in the same way or differently with hydroxy, halogen, $C_1$-$C_6$-alkoxy, $C_1$-$C_6$-alkylthio, amino, cyano, $C_1$-$C_6$-alkyl, $C_2$-$C_6$-alkenyl, $C_3$-$C_7$-cycloalkyl, $C_1$-$C_6$-alkoxy-$C_1$-$C_6$-alkyl, —$NHC_1$-$C_6$-alkyl, —$N(C_1$-$C_6$-alkyl$)_2$, —$SO(C_1$-$C_6$-alkyl), —$SO_2$ ($C_1$-$C_6$-alkyl), $C_1$-$C_6$-alkanoyl, —$CONR^3R^4$, —$COR^5$, $C_1$-$C_6$-alkoxyOAc, phenyl or with the group $R^6$, whereby the phenyl itself optionally can be substituted in one or more places in the same way or differently with halogen, hydroxy, $C_1$-$C_6$-alkyl, $C_1$-$C_6$-alkoxy or with the group —$CF_3$ or —$OCF_3$, $R^3$ and $R^4$, in each case independently of one another, stand for hydrogen, hydroxy, $C_1$-$C_6$-alkoxy, or for $C_1$-$C_6$-alkyl that is optionally substituted in one or more places in the same way or differently with hydroxy, $C_1$-$C_6$-alkoxy, $C_1$-$C_6$-alkylthio, —$N(C_1$-$C_6$-alkyl$)_2$, the group $R^6$, or —$N(C_1$-$C_6$-alkyl)$R^6$, or $R^3$ and $R^4$ together form a $C_3$-$C_7$-cycloalkyl ring that optionally can be interrupted by one or more nitrogen, oxygen and/or sulfur atoms and/or can be interrupted by one or more =C=O groups in the ring and/or one or more possible double bonds optionally can be contained in the ring, $R^5$ stands for hydroxy, benzoxy, $C_1$-$C_6$-alkyl, $C_1$-$C_6$-alkylthio or $C_1$-$C_6$-alkoxy, $R^6$ stands for a benzylthio, phenyloxy, or $C_3$-$C_7$-cycloalkyl ring that is optionally substituted in one or more places in the same way or differently with halogen, hydroxy, $C_1$-$C_6$-alkyl, $C_1$-$C_6$-alkoxy or —$SO_2NR^3R^4$, whereby the $C_3$-$C_7$-cycloalkyl ring has the meaning that is indicated under $R^2$, $R^7$ stands for $C_1$-$C_6$-alkyl, $C_2$-$C_6$-alkenyl, $C_2$-$C_6$-alkinyl, benzyl, or $C_3$-$C_7$-cycloalkyl, whereby the $C_3$-$C_7$-cycloalkyl ring has the meaning that is indicated under $R^2$, or for the group —$NR^3R^4$, or for $C_1$-$C_{10}$-alkyl, $C_2$-$C_{10}$-alkenyl, $C_2$-$C_{10}$-alkinyl or $C_3$-$C_7$-cycloalkyl that is optionally substituted in one or more places in the same way or differently with hydroxy, $C_1$-$C_6$-alkoxy, halogen, phenyl, —$NR^3R^4$ or phenyl, which itself can be substituted in one or more places in the same way or differently with halogen, hydroxy, $C_1$-$C_6$-alkyl, $C_1$-$C_6$-alkoxy, halo-$C_1$-$C_6$-alkyl, or halo-$C_1$-$C_6$-alkoxy, or $R^7$ stands for phenyl, which itself optionally can be substituted in one or more places in the same way or differently with halogen, hydroxy, $C_1$-$C_6$-alkyl or $C_1$-$C_6$-alkoxy, halo-$C_1$-$C_6$-alkyl, or halo-$C_1$-$C_6$-alkoxy, and n stands for 0 or 1, if n=0, then X stands for halogen, as well as isomers, diastereomers, enantiomers and salts thereof, overcome the known drawbacks.

Alkyl is defined in each case as a straight-chain or branched alkyl radical, such as, for example, methyl, ethyl, propyl, isopropyl, butyl, isobutyl, sec-butyl, tert-butyl, pentyl, isopentyl, hexyl, heptyl, octyl, nonyl or decyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Cycloalkyl is defined in each case as cyclopropyl, cyclobutyl, cyclopentyl, cyclohexyl and cycloheptyl.

The ring systems, in which optionally one or more possible double bonds can be contained in the ring, are defined as, for example, cycloalkenyls, such as cyclopropenyl, cyclobutenyl, cyclopentenyl, cyclohexenyl, or cycloheptenyl, whereby the linkage both to the double bond and to the single bonds can be carried out.

Halogen is defined in each case as fluorine, chlorine, bromine or iodine.

The alkenyl substituents in each case are straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, ethinyl, prop-1-in-1-yl, but-1-in-1-yl, but-2-in-1-yl, but-3-en-1-yl, and allyl.

The alkinyl substituents are in each case straight-chain or branched, whereby, for example, the following radicals are meant: propargyl, propin-1-yl, propin-2-yl, but-1-in-1-yl, but-1-in-2-yl, but-2-in-1-yl, but-2-in-2-yl, 2-methyl-prop-2-in-1-yl, 2-methyl-prop-1-in-1-yl, but-1-in-3-yl, ethinyl, prop-1-in-1-yl, but-1-in-1-yl, but-2-in-1-yl, and but-3-in-1-y.

Aryl is defined as an aryl radical, in each case with 6-12 carbon atoms, such as, for example, naphthyl, biphenyl and especially phenyl.

Heteroaryl is defined as a heteroaryl radical that in each case can also be benzocondensed. For example, thiophene, furan, oxazole, thiazole, imidazole, pyrazole, triazole, thia-4H-pyrazole and benzo derivatives thereof can be mentioned as 5-ring heteroatoms, and pyridine, pyrimidine, triazine, quinoline, isoquinoline and benzo derivatives can be mentioned as 6-ring heteroaromatic compounds.

If an acid group is included, the physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropane diol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, i.a.

Those compounds of general formula I in which

Q stands for the group

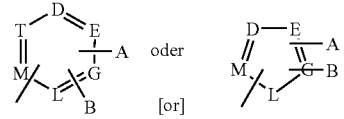

oder [or]

D, E, G,

L, M and T, in each case independently of one another, stand for carbon, oxygen, nitrogen or sulfur, whereby at least one heteroatom must be contained in the ring, $R^1$ stands for hydrogen, halogen, $C_1$-$C_6$-alkyl, $C_1$-$C_6$-alkinyl, nitro, cyano, heteroaryl or for the group —$COR^5$, —$OCF_3$, —S—$CF_3$ or —$SO_2CF_3$, $R^2$ stands for hydrogen, $C_1$-$C_{10}$-alkyl, $C_2$-$C_{10}$-alkenyl, $C_2$-$C_{10}$-alkinyl, aryl, heteroaryl or $C_3$-$C_7$-cycloalkyl or for $C_1$-$C_{1-10}$-alkyl, $C_2$-$C_{10}$-alkenyl, $C_2$-$C_{10}$-alkinyl, aryl, heteroaryl or $C_3$-$C_7$-cycloalkyl that is optionally substituted in one or more places in the same way or differently with hydroxy, halogen, $C_1$-$C_6$-alkoxy, $C_1$-$C_6$-alkylthio, amino, cyano, $C_1$-$C_6$-alkyl, $C_2$-$C_6$-alkenyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_3$-$C_7$-cycloalkyl, —$NHC_1$-$C_6$-alkyl, —$NHC_3$-$C_7$-cycloalkyl, —$N(C_1$-$C_6$-alkyl)$_2$, —$SO(C_1$-$C_6$-alkyl), —$SO_2$ ($C_1$-$C_6$-alkyl), $C_1$-$C_6$-alkanoyl, —$CONR^3R^4$, —$COR^5$, $C_1$-$C_6$-alkylOAc, phenyl or with the group —$R^6$, the ring of the $C_3$-$C_7$-cycloalkyl optionally can be interrupted by one or more nitrogen, oxygen and/or sulfur atoms and/or can be interrupted by one or more =C=O groups in the ring and/or optionally one or more possible double bonds can be contained in the ring, and the phenyl, aryl or $C_3$-$C_7$-cycloalkyl itself optionally can be substituted in one or more places in the same way or differently with halogen, hydroxy, $C_1$-$C_6$-alkyl, or $C_1$-$C_6$-alkoxy, or with the group —$CF_3$ or —$OCF_3$, X stands for halogen, oxygen, sulfur or for the group —NH— or —$N(C_1$-$C_3$-alkyl), or X and $R^2$ together form a $C_3$-$C_{10}$-cycloalkyl ring, which optionally can contain one or more heteroatoms and optionally can be substituted in one or more places with hydroxy, $C_1$-$C_6$-alkyl, hydroxy-$C_1$-$C_6$-alkyl or halogen, A and B, in each case independently of one another, stand for hydrogen, hydroxy, halogen, or for the group —$SR^7$, —$S(O)R^7$, —$SO_2$ $R^7$, —$NHSO_2$ $R^7$, —CH(OH)$R^7$, —$CR^7$ (OH)—$R^7$, $C_1$-$C_6$-alkylP(O)$OR^3OR^4$ or —$COR^7$, $R^3$ and $R^4$, in each case independently of one another, stand for hydrogen, hydroxy, $C_1$-$C_6$-alkoxy, hydroxy-$C_1$-$C_6$-alkyl, or for $C_1$-$C_6$-alkyl that is optionally substituted in one or more places in the same way or differently with hydroxy, $C_1$-$C_6$-alkoxy, $C_1$-$C_6$-alkylthio, —N($C_{1-6}$-alkyl)$_2$, the group $R^6$, or —N($C_1$-$C_6$-alkyl)$R^6$, $R^5$ stands for hydroxy, benzoxy, $C_1$-$C_6$-alkyl, $C_1$-$C_6$-alkylthio or $C_1$-$C_6$-alkoxy, $R^6$ stands for a benzylthio, phenyloxy or $C_3$-$C_7$-cycloalkyl ring that is optionally substituted in one or more places in the same way or differently with halogen, hydroxy, $C_1$-$C_6$-alkyl, $C_1$-$C_6$-alkoxy or —$SO_2NR^3R^4$, whereby the $C_3$-$C_7$-cycloalkyl ring has the meaning that is indicated under $R^2$, $R^7$ stands for $C_1$-$C_6$-alkyl, $C_2$-$C_6$-alkenyl, $C_2$-$C_6$-alkinyl, benzyl, or $C_3$-$C_7$-cycloalkyl, whereby the $C_3$-$C_7$-cycloalkyl ring has the meaning that is indicated under $R^2$, or for the group —$NR^3R^4$, or for $C_1$-$C_{10}$-alkyl, $C_2$-$C_{10}$-alkenyl, $C_2$-$C_{10}$-alkinyl or $C_3$-$C_7$-cycloalkyl that is optionally substituted in one or more places in the same way or differently with hydroxy, $C_1$-$C_6$-alkoxy, halogen, phenyl, —$NR^3R^4$ or phenyl, which itself can be substituted in one or more places in the same way or differently with halogen, hydroxy, $C_1$-$C_6$-alkyl, $C_1$-$C_6$-alkoxy, halo-$C_1$-$C_6$-alkyl, or halo-$C_1$-$C_6$-alkoxy, or $R^7$ stands for phenyl, which itself optionally can be substituted in one or more places in the same way or differently with halogen, hydroxy, $C_1$-$C_6$-alkyl or $C_1$-$C_6$-alkoxy, halo-$C_1$-$C_6$-alkyl, or halo-$C_1$-$C_6$-alkoxy, and n stands for 0 or 1, if n=0, then X stands for halogen, as well as isomers, diastereomers, enantiomers and salts thereof are especially effective.

Those compounds of general formula I in which Q stands for the group

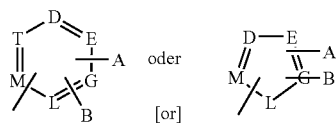

D, E, G,

L, M and T, in each case independently of one another, stand for carbon, oxygen, nitrogen or sulfur, whereby at least one heteroatom must be contained in the ring, $R^1$ stands for hydrogen, halogen, $C_1$-$C_6$-alkyl, $C_1$-$C_6$-alkinyl, nitro, cyano, heteroaryl or for the group —$COR^5$, —$OCF_3$, —S—$CF_3$ or —$SO_2CF_3$, $R^2$ stands for hydrogen, $C_1$-$C_{10}$-alkyl, $C_2$-$C_{10}$-alkenyl, $C_2$-$C_{10}$-alkinyl, aryl, heteroaryl or $C_3$-$C_7$-cycloalkyl or for $C_1$-$C_{10}$-alkyl, $C_2$-$C_{10}$-alkenyl, $C_2$-$C_{10}$-alkinyl, aryl, heteroaryl or $C_3$-$C_7$-cycloalkyl that is optionally substituted in one or more places in the same way or differently with hydroxy, halogen, $C_1$-$C_6$-alkoxy, $C_1$-$C_6$-alkylthio, amino, cyano, $C_1$-$C_6$-alkyl, $C_2$-$C_6$-alkenyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_3$-$C_7$-cycloalkyl, —$NHC_1$-$C_6$-alkyl, —$NHC_3$-$C_7$-cycloalkyl, —N($C_1$-$C_6$-alkyl)$_2$, —SO($C_1$-$C_6$-alkyl), —$SO_2$ ($C_1$-$C_6$-alkyl), $C_1$-$C_6$-alkanoyl, —$CONR^3R^4$, —$COR^5$, $C_1$-$C_6$-alkylOAc, phenyl or with the group —$R^6$, the ring of the $C_3$-$C_7$-cycloalkyl optionally can be interrupted by one or more nitrogen, oxygen and/or sulfur atoms and/or can be interrupted by one or more =C=O groups in the ring and/or optionally one or more possible double bonds can be contained in the ring, and the phenyl, aryl or $C_3$-$C_7$-cycloalkyl itself optionally can be substituted in one or more places in the same way or differently with halogen, hydroxy, $C_1$-$C_6$-alkyl, $C_1$-$C_6$-alkoxy, or with the group —$CF_3$ or —$OCF_3$, X stands for halogen, oxygen, sulfur or for the group —NH— or —N($C_1$-$C_3$-alkyl)-, or X and $R^2$ together form a $C_3$-$C_{10}$-cycloalkyl ring, which optionally can contain one or more heteroatoms and optionally can be substituted in one or more places with hydroxy, $C_1$-$C_6$-alkyl, hydroxy-$C_1$-$C_6$-alkyl or halogen, A and B, in each case independently of one another, stand for hydrogen, hydroxy, halogen, or for the group —$SR^7$, —$S(O)R^7$, —$SO_2$ $R^7$, —$NHSO_2$ $R^7$, —CH(OH)$R^7$, —$CR^7$ (OH)—$R^7$, $C_1$-$C_6$-alkylP(O)$OR^3OR^4$ or —$COR^7$, $R^3$ and $R^4$, in each case independently of one another, stand for hydrogen, hydroxy, $C_1$-$C_6$-alkoxy, hydroxy-$C_1$-$C_6$-alkyl, or for $C_1$-$C_6$-alkyl that is optionally substituted in one or more places in the same way or differently with hydroxy, $C_{1-6}$-alkoxy, $C_1$-$C_6$-alkylthio, —N($C_1$-$C_6$-alkyl)$_2$, the group $R^6$ or —N($C_1$-$C_6$-alkyl)$R^6$, $R^5$ stands for hydroxy, benzoxy, $C_1$-$C_6$-alkyl, $C_1$-$C_6$-alkylthio or $C_1$-$C_6$-alkoxy, $R^6$ stands for a benzylthio, phenyloxy, or $C_3$-$C_7$-cycloalkyl ring that is optionally substituted in one or more places in the same way or differently with halogen, hydroxy, $C_1$-$C_6$-alkyl, $C_1$-$C_6$-alkoxy or —$SO_2NR^3R^4$, whereby the $C_3$-$C_7$-cycloalkyl ring has the meaning that is indicated under $R^2$, $R^7$ stands for $C_1$-$C_6$-alkyl, $C_2$-$C_6$-alkenyl, $C_2$-$C_6$-alkinyl, benzyl, $C_3$-$C_7$-cycloalkyl, whereby the $C_3$-$C_7$-cycloalkyl ring has the meaning that is indicated under $R^2$, or for the group —$NR^3R^4$, or for $C_1$-$C_{10}$-alkyl, $C_2$-$C_{10}$-alkenyl, $C_2$-$C_{10}$-alkinyl or $C_3$-$C_7$-cycloalkyl that is substituted in one or more places in the same way or differently with hydroxy, $C_1$-$C_6$-alkoxy, halogen, phenyl, —$NR^3R^4$ or phenyl, which itself can be substituted in one or more places in the same way or differently with halogen, hydroxy, $C_1$-$C_6$-alkyl, $C_1$-$C_6$-alkoxy, halo-$C_1$-$C_6$-alkyl, or halo-$C_1$-$C_6$-alkoxy, or $R^7$ stands for phenyl, which itself can be substituted in one or more places in the same way or differently with halogen, hydroxy, $C_1$-$C_6$-alkyl or $C_1$-$C_6$-alkoxy, halo-$C_1$-$C_6$-alkyl, or halo-$C_1$-$C_6$-alkoxy, and n stands for 0 or 1, if n=0, then X stands for halogen, as well as isomers, diastereomers, enantiomers and salts thereof, have proven quite especially effective.

Those compounds of general formula I, in which
Q stands for the group

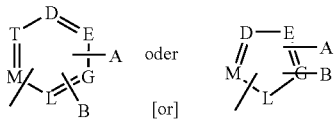

D, E, G,
L, M and T, in each case independently of one another, stand for carbon, oxygen, nitrogen or sulfur, whereby at least one heteroatom must be contained in the ring,
$R^1$ stands for hydrogen, halogen, $C_1$-$C_6$-alkyl, $C_1$-$C_6$-alkinyl, nitro, cyano, heteroaryl or for the group —$COR^5$, —$OCF_3$, —S—$CF_3$ or —$SO_2CF_3$,
$R^2$ stands for hydrogen, $C_2$-$C_{10}$-alkinyl, $C_3$-$C_7$-cycloalkyl or for $C_1$-$C_{10}$-alkyl, phenyl, or $C_3$-$C_7$-cycloalkyl that is optionally substituted in one or more places in the same way or differently with hydroxy, $C_1$-$C_6$-alkyl, $C_1$-$C_6$-alkoxy, $C_3$-$C_7$-cycloalkyl, —$N(C_1$-$C_6$-alkyl$)_2$, —$NHC_3$-$C_7$-cycloalkyl, —$COR^5$, phenyl or with the group $R^6$, whereby the $C_3$-$C_7$-cycloalkyl ring has the meaning that is indicated under $R^2$ of claims 1 to 3, and phenyl or $C_3$-$C_7$-cycloalkyl optionally is substituted with hydroxy,
X stands for halogen, oxygen, sulfur or for the group —NH— or for —N($C_1$-$C_3$-alkyl)-
or
Those compounds of general formula I, in which
Q stands for the group

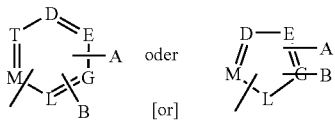

D, E, G,
L, M and T, in each case independently of one another, stand for carbon, oxygen, nitrogen or sulfur, whereby at least one heteroatom must be contained in the ring,
$R^1$ stands for halogen,
$R^2$ stands for hydrogen, $C_2$-$C_{10}$-alkinyl, or for $C_1$-$C_{10}$-alkyl, phenyl, or $C_3$-$C_7$-cycloalkyl that is optionally substituted in one or more places in the same way or differently with hydroxy, $C_1$-$C_6$-alkyl, $C_1$-$C_6$-alkoxy, $COR^5$, $C_3$-$C_7$-cycloalkyl, —$N(C_1$-$C_6$-alkyl$)_2$, —$NHC_3$-$C_7$-cycloalkyl or phenyl, whereby the $C_3$-$C_7$-cycloalkyl ring has the meaning that is indicated under $R^2$ of claims 1 to 3, and phenyl or $C_3$-$C_7$-cycloalkyl optionally can be substituted with hydroxy,
X stands for halogen, oxygen, sulfur or for the group —NH— or for —N($C_1$-$C_3$-alkyl)-,
or
X and $R^2$ together form a $C_3$-$C_{10}$-cycloalkyl ring, which optionally can contain one or more heteroatoms and optionally can be substituted in one or more places with hydroxy, $C_1$-$C_6$-alkyl, hydroxy-$C_1$-$C_6$-alkyl or halogen,
A and B, in each case independently of one another, stand for hydrogen, halogen, or for the group —$SR^7$, —S(O)$R^7$, or —$SO_2R^7$, $R^3$ and $R^4$, in each case independently of one another, stand for hydrogen or hydroxy, or for $C_1$-$C_6$-alkyl that is optionally substituted in one or more places in the same way or differently with hydroxy, $C_1$-$C_6$-alkoxy, $C_1$-$C_6$-alkylthio, —$N(C_1$-$C_6$-alkyl$)_2$, the group $R^6$, or —$N(C_1$-$C_6$-alkyl)$R^6$,
$R^5$ stands for $C_1$-$C_6$-alkyl,
$R^6$ stands for a benzylthio, phenyloxy or a $C_3$-$C_7$-cycloalkyl ring that is optionally substituted in one or more places in the same way or differently with halogen, hydroxy, $C_1$-$C_6$-alkyl, $C_1$-$C_6$-alkoxy or —$SO_2NR^3R^4$, whereby the $C_3$-$C_7$-cycloalkyl ring has the meaning that is indicated under $R^2$ of claims 1 to 3,
$R^7$ stands for $C_1$-$C_6$-alkyl, benzyl, or for the group —$NR^3R^4$, and
N stands for 0 or 1, if n=0, then X stands for halogen,
as well as isomers, diastereomers, enantiomers and salts thereof, are especially valuable.

Compounds of general formula I, in which
Q stands for pyridine, thiophene, 1,3,4-thiadiazole, or 1,2,4-triazole,
$R^1$ stands for bromine or chlorine,
$R^2$ stands for hydrogen, $C_2$-$C_{10}$-alkinyl or for $C_1$-$C_{10}$-alkyl, phenyl or $C_3$-$C_7$-cycloalkyl that is optionally substituted in one or more places in the same way or differently with hydroxy, $C_1$-$C_6$-alkyl, $C_1$-$C_6$-alkoxy, $COR^5$, $C_3$-$C_7$-cycloalkyl, —$N(C_1$-$C_6$-alkyl$)_2$, —$NHC_3$-$C_7$-cycloalkyl or phenyl, whereby the $C_3$-$C_7$-cycloalkyl ring has the meaning that is indicated under $R^2$ of claims 1 to 3, and phenyl or $C_3$-$C_7$-cycloalkyl is optionally substituted with hydroxy,
X stands for chlorine, oxygen, sulfur or for the group —NH— or for —N($C_1$-$C_3$-alkyl)-,
or
X and $R^2$ together form a piperidine or a pyrrolidine ring, which optionally can be substituted in one or more places with hydroxy, $C_1$-$C_6$-alkyl, hydroxy-$C_1$-$C_6$-alkyl or halogen,
A and B, in each case independently of one another, stand for hydrogen, chlorine or for the group —$SR^7$, —S(O)$R^7$ or —$SO_2R^7$,
$R^3$ and $R^4$, in each case independently of one another, stand for hydrogen or for $C_1$-$C_6$-alkyl that is optionally substituted in one or more places in the same way or differently with hydroxy, $C_1$-$C_6$-alkoxy, $C_1$-$C_6$-alkylthio, —$N(C_1$-$C_6$-alkyl$)_2$, the group $R^6$ or —$N(C_1$-$C_6$-alkyl)-$R^6$,
$R^5$ stands for $C_1$-$C_6$-alkyl,
$R^6$ stands for $C_3$-$C_7$-cycloalkyl that is optionally substituted in one or more places in the same way or differently with halogen, hydroxy, $C_1$-$C_6$-alkyl, $C_1$-$C_6$-alkoxy or —$SO_2NR^3R^4$, whereby the $C_3$-$C_7$-cycloalkyl ring has the meaning that is indicated under $R^2$ of claims 1 to 3, benzylthio, furan, imidazole, morpholine, oxolane, phenyl, phenyloxy, piperidine, pyridine, pyrazine, pyrrolidine or y-butyrolactam ring,
$R^7$ stands for $C_1$-$C_6$-alkyl, benzyl or for the group —$NR^3R^4$, and
n stands for 0 or 1, if n=0, then X stands for chlorine,
as well as isomers, diastereomers, enantiomers and salts thereof, are quite especially valuable.

In addition, it has been found that compounds of general formula I$_f$

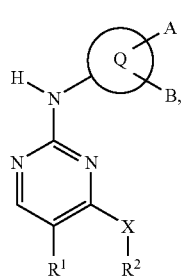

(I$_f$)

in which

Q stands for the group

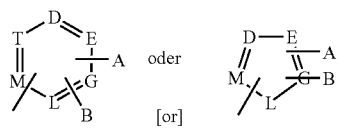

D, E, G,

L, M and T, in each case independently of one another, stand for carbon, oxygen, nitrogen or sulfur, whereby at least one heteroatom must be contained in the ring, R$^1$ stands for hydrogen, halogen, C$_1$-C$_6$-alkyl, C$_1$-C$_6$-alkinyl, nitro, cyano, heteroaryl or for the group —COR$^5$, —OCF$_3$—S—CF$_3$ or —SO$_2$CF$_3$, R$^2$ stands for hydrogen, C$_1$-C$_{10}$-alkyl, C$_2$-C$_{10}$-alkenyl, C$_2$-C$_{10}$-alkinyl, aryl, heteroaryl or C$_3$-C$_7$-cycloalkyl or for C$_1$-C$_{10}$-alkyl, C$_2$-C$_{10}$-alkenyl, C$_2$-C$_{10}$-alkinyl, aryl, heteroaryl or C$_3$-C$_7$-cycloalkyl that is substituted in one or more places in the same way or differently with hydroxy, halogen, C$_1$-C$_6$-alkoxy, C$_1$-C$_6$-alkylthio, amino, cyano, C$_1$-C$_6$-alkyl, C$_2$-C$_6$-alkenyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —NHC$_1$-C$_6$-alkyl, NHC$_3$-C$_7$-cycloalkyl, —N(C$_1$-C$_6$-alkyl)$_2$, —SO(C$_1$-C$_6$-alkyl), —SO$_2$ (C$_1$-C$_6$-alkyl), C$_1$-C$_6$-alkanoyl, —CONR$^3$R$^4$, —COR$^5$, C$_1$-C$_6$-alkylOAc, phenyl or with the group —R$^6$, and the phenyl itself optionally can be substituted in one or more places in the same way or differently with halogen, hydroxy, C$_1$-C$_6$-alkyl, or C$_1$-C$_6$-alkoxy, or with the group —CF$_3$ or —OCF$_3$, and the ring of the C$_3$-C$_7$-cycloalkyl optionally can be interrupted by one or more nitrogen, oxygen and/or sulfur atoms and/or can be interrupted by one or more =C=O groups in the ring and/or optionally one or more possible double bonds can be contained in the ring, X stands for halogen, oxygen, sulfur or for the group —NH— or —N(C$_1$-C$_3$-alkyl)-, or X and R$^2$ together form a C$_3$-C$_{10}$-cycloalkyl ring, which optionally can contain one or more heteroatoms and optionally can be substituted in one or more places with hydroxy, C$_1$-C$_6$-alkyl, hydroxy-C$_1$-C$_6$-alkyl or halogen, A and B, in each case independently of one another, stand for hydrogen, halogen, hydroxy, or for the group —SR$^7$, —S(O)R$^7$, or —SO$_2$ R$^7$, R$^3$ and R$^4$, in each case independently of one another, stand for hydrogen, hydroxy, C$_1$-C$_6$-alkoxy, hydroxy-C$_1$-C$_6$-alkyl, or for C$_1$-C$_6$-alkyl that is optionally substituted in one or more places in the same way or differently with hydroxy, C$_1$-C$_6$-alkoxy, C$_1$-C$_6$-alkylthio, —N(C$_1$-C$_6$-alkyl)$_2$, the group R$^6$, or —N(C$_1$-C$_6$-alkyl)R$^6$, R$^5$ stands for hydroxy, benzoxy, C$_1$-C$_6$-alkyl, C$_1$-C$_6$-alkylthio or C$_1$-C$_6$-alkoxy, R$^6$ stands for a benzylthio, phenyloxy or C$_3$-C$_7$-cycloalkyl ring that is optionally substituted in one or more places in the same way or differently with halogen, hydroxy, C$_1$-C$_6$-alkyl, C$_1$-C$_6$-alkoxy or —SO$_2$NR$^3$R$^4$, whereby the C$_3$-C$_7$-cycloalkyl ring has the meaning that is indicated under R$^2$ of claims 1 to 3, R$^7$ stands for C$_1$-C$_6$-alkyl, C$_2$-C$_6$-alkenyl, C$_2$-C$_6$-alkinyl, benzyl, or C$_3$-C$_7$-cycloalkyl, whereby the C$_3$-C$_7$-cycloalkyl ring has the meaning that is indicated under R$^2$ of claims 1 to 3 or stands for the group —NR$^3$R$^4$, and n stands for 0 or 1, if n=0, then X stands for halogen, as well as isomers, diastereomers, enantiomers and salts thereof, are especially effective.

X and R$^2$ together form a C$_3$-C$_{10}$-cycloalkyl ring, which optionally can contain one or more heteroatoms and optionally can be substituted in one or more places with hydroxy, C$_1$-C$_6$-alkyl, hydroxy-C$_1$-C$_6$-alkyl or halogen, A and B, in each case independently of one another, stand for hydrogen, hydroxy, halogen, or for the group —SR$^7$, —S(O)R$^7$, —SO$_2$ R$^7$, —NHSO$_2$R$^7$, —CH(OH)R$^7$, —CR$^7$ (OH)—R$^7$, C$_1$-C$_6$-alkylP(O)OR$^3$OR$^4$ or —COR$^7$, or A and B together form a C$_3$-C$_7$-cycloalkyl ring that optionally can be interrupted by one or more nitrogen, oxygen and/or sulfur atoms and/or can be interrupted by one or more =C=O groups in the ring and/or optionally one or more possible double bonds can be contained in the ring, and the C$_3$-C$_7$-cycloalkyl ring optionally can be substituted in one or more places in the same way or differently with hydroxy, halogen, C$_1$-C$_6$-alkoxy, C$_1$-C$_6$-alkylthio, amino, cyano, C$_1$-C$_6$-alkyl, C$_2$-C$_6$-alkenyl, C$_3$-C$_7$-cycloalkyl, C$_1$-C$_6$-alkoxy-C$_1$-C$_6$-alkyl, —NHC$_1$-C$_6$-alkyl, —N(C$_1$-C$_6$-alkyl)$_2$, —SO(C$_1$-C$_6$-alkyl), —SO$_2$ (C$_1$-C$_6$-alkyl), C$_1$-C$_6$-alkanoyl, —CONR$^3$R$^4$, —COR$^5$, C$_1$-C$_6$-alkoxyOAc, phenyl or with the group R$^6$, whereby the phenyl itself optionally can be substituted in one or more places in the same way or differently with halogen, hydroxy, C$_1$-C$_6$-alkyl, C$_1$-C$_6$-alkoxy or with the group —CF$_3$ or —OCF$_3$, R$^3$ and R$^4$, in each case independently of one another, stand for hydrogen, hydroxy, C$_1$-C$_6$-alkoxy, hydroxy-C$_{1-6}$-alkyl, or for C$_1$-C$_6$-alkyl that is optionally substituted with the group R$^6$, or R$^3$ and R$^4$ together form a C$_3$-C$_7$-cycloalkyl ring that optionally can be interrupted by one or more nitrogen, oxygen and/or sulfur atoms and/or can be interrupted by one or more =C=O groups in the ring and/or optionally one or more possible double bonds can be contained in the ring, R$^5$ stands for hydroxy, benzoxy, C$_1$-C$_6$-alkyl, C$_1$-C$_6$-alkylthio or C$_1$-C$_6$-alkoxy, R[6] stands for a $C_3$-$C_7$-cycloalkyl ring that is optionally substituted in one or more places in the same way or differently with $C_1$-$C_6$-alkyl or hydroxy, whereby the ring has the above-indicated meaning, R[7] stands for $C_1$-$C_6$-alkyl, $C_2$-$C_6$-alkenyl, $C_2$-$C_6$-alkinyl, benzyl, or $C_3$-$C_7$-cycloalkyl, with the above-indicated meaning, or for the group —NR[3]R[4], or for $C_1$-$C_{10}$-alkyl, $C_2$-$C_{10}$-alkenyl, $C_2$-$C_{10}$-alkinyl or $C_3$-$C_7$-cycloalkyl that is substituted in one or more places in the same way or differently with hydroxy, $C_1$-$C_6$-alkoxy, halogen, phenyl, —NR[3]R[4] or phenyl, which itself can be substituted in one or more places in the same way or differently with halogen, hydroxy, $C_1$-$C_6$-alkyl, $C_1$-$C_6$-alkoxy, halo-$C_1$-$C_6$-alkyl, or halo-$C_1$-$C_6$-alkoxy, or R[7] stands for phenyl, which itself can be substituted in one or more places in the same way or differently with halogen, hydroxy, $C_1$-$C_6$-alkyl or $C_1$-$C_6$-alkoxy, halo-$C_1$-$C_6$-alkyl, or halo-$C_1$-$C_6$-alkoxy, as well as isomers, diastereomers, enantiomers and salts thereof, overcome the known drawbacks.

In particular, compounds of general formula $I_f$, in which Q stands for the group

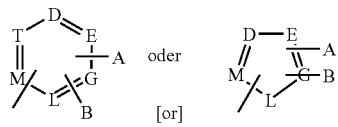

D, E, G,

L, M and T, in each case independently of one another, stand for carbon, oxygen, nitrogen or sulfur, whereby at least one heteroatom must be contained in the ring, R[1] stands for halogen, R[2] stands for hydrogen, $C_2$-$C_{10}$-alkinyl, $C_3$-$C_7$-cycloalkyl or for $C_1$-$C_{10}$-alkyl or $C_3$-$C_7$-cycloalkyl that is substituted in one or more places in the same way or differently with hydroxy, $C_1$-$C_6$-alkyl, $C_1$-$C_6$-alkoxy, COR[5], —N($C_1$-$C_6$-alkyl)$_2$, —NH$C_3$-$C_7$-cycloalkyl or $C_3$-$C_7$-cycloalkyl, X stands for halogen, oxygen, sulfur or for the group —NH— or for —N($C_1$-$C_3$-alkyl)-, or X and R[2] together form a $C_3$-$C_{10}$-cycloalkyl ring, which optionally can contain one or more heteroatoms and optionally can be substituted in one or more places with hydroxy, $C_1$-$C_6$-alkyl, hydroxy-$C_1$-$C_6$-alkyl or halogen, A and B, in each case independently of one another, stand for hydrogen, halogen, or for the group —SR[7], —S(O)R[7], or —SO$_2$R[7], R[3] and R[4], in each case independently of one another, stand for hydrogen, hydroxy, hydroxy-$C_1$-$C_6$-alkyl, or for $C_1$-$C_6$-alkyl that is optionally substituted with the group R[6], R[5] stands for $C_1$-$C_6$-alkyl, R[6] stands for a $C_3$-$C_7$-cycloalkyl ring that is optionally substituted in one or more places in the same way or differently with $C_1$-$C_6$-alkyl or hydroxy, whereby the ring has the above-indicated meaning, R[7] stands for $C_1$-$C_6$-alkyl, benzyl, or for the group —NR[3]R[4], as well as isomers, diastereomers, enantiomers and salts thereof, are effective.

In addition, compounds of general formula $I_f$

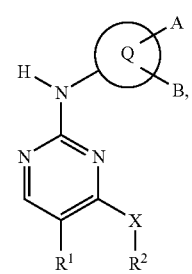

(I$_f$)

in which

Q stands for the group

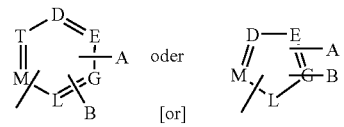

D, E, G,

L, M and T, in each case independently of one another, stand for carbon, oxygen, nitrogen or sulfur, whereby at least one heteroatom must be contained in the ring, R[1] stands for hydrogen, halogen, $C_1$-$C_6$-alkyl, $C_1$-$C_6$-alkinyl, nitro, cyano, heteroaryl or for the group —COR[5], —OCF$_3$, —S—CF$_3$ or —SO$_2$CF$_3$, R[2] stands for $C_1$-$C_{10}$-alkyl, $C_2$-$C_{10}$-alkenyl, $C_2$-$C_{10}$-alkinyl, aryl, heteroaryl or $C_3$-$C_7$-cycloalkyl or for $C_1$-$C_{10}$-alkyl, $C_2$-$C_{10}$-alkenyl, $C_2$-$C_{10}$-alkinyl, aryl, heteroaryl or $C_3$-$C_7$-cycloalkyl that is substituted in one or more places in the same way or differently with hydroxy, halogen, $C_1$-$C_6$-alkoxy, $C_1$-$C_6$-alkylthio, amino, cyano, $C_1$-$C_6$-alkyl, $C_2$-$C_6$-alkenyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —NH$C_1$-$C_6$-alkyl, —N($C_1$-$C_6$-alkyl)$_2$, —SO($C_1$-$C_6$-alkyl), —SO$_2$ ($C_1$-$C_6$-alkyl), $C_1$-$C_6$-alkanoyl, —CONR[3]R[4], —COR[5], $C_1$-$C_6$-alkylOAc, phenyl or with the group —R[6], and the phenyl itself optionally can be substituted in one or more places in the same way or differently with halogen, hydroxy, $C_1$-$C_6$-alkyl, or $C_1$-$C_6$-alkoxy, or with the group —CF$_3$ or —OCF$_3$, and the ring of the $C_3$-$C_7$-cycloalkyl optionally can be interrupted by one or more nitrogen, oxygen and/or sulfur atoms and/or can be interrupted by one or more =C=O groups in the ring and/or optionally one or more possible double bonds can be contained in the ring, X stands for oxygen, sulfur or for the group —NH—, A and B, in each case independently of one another, stand for hydrogen, hydroxy, halogen, or for the group —SR[7], —S(O)R[7], —SO$_2$ R[7], —NHSO$_2$ R[7], —CH(OH)R[7], —CR[7](OH)—R[7], $C_1$-$C_6$-alkylP(O)OR[3]OR[4] or —COR[7], or A and B together form a $C_3$-$C_7$-cycloalkyl ring that optionally can be interrupted by one or more nitrogen, oxygen and/or sulfur atoms and/or can be interrupted by one or more =C=O groups in the ring and/or optionally one or more possible double bonds can be contained in the ring, and the $C_3$-$C_7$-cycloalkyl ring optionally can be substituted in one or more places in the same way or differently with hydroxy, halogen, $C_1$-$C_6$-alkoxy, $C_1$-$C_6$-alkylthio, amino, cyano, $C_1$-$C_6$-alkyl, $C_2$-$C_6$-alkenyl, $C_3$-$C_7$-cycloalkyl, $C_1$-$C_6$-alkoxy-$C_1$-$C_6$-alkyl, —NHC$_1$-$C_6$-alkyl, —N($C_1$-$C_6$-alkyl)$_2$, —SO($C_1$-$C_6$-alkyl), —SO$_2$ ($C_1$-$C_6$-alkyl), $C_1$-$C_6$-alkanoyl, —CONR$^3$R$^4$, —COR$^5$, $C_1$-$C_6$-alkoxyOAc, phenyl or with the group R$^6$, whereby the phenyl itself optionally can be substituted in one or more places in the same way or differently with halogen, hydroxy, $C_1$-$C_6$-alkyl, $C_1$-$C_6$-alkoxy or with the group —CF$_3$ or —OCF$_3$, R$^3$ and R$^4$, in each case independently of one another, stand for hydrogen, hydroxy, $C_1$-$C_6$-alkoxy, hydroxy-$C_1$-$C_6$-alkyl, $C_1$-$C_6$-alkyl or for the group —NR$^3$R$^4$, or R$^3$ and R$^4$ together form a $C_3$-$C_7$-cycloalkyl ring that optionally can be interrupted by one or more nitrogen, oxygen and/or sulfur atoms and/or can be interrupted by one or more =C=O groups in the ring and/or optionally one or more possible double bonds can be contained in the ring, R$^5$ stands for hydroxy, benzoxy, $C_1$-$C_6$-alkylthio or $C_1$-$C_6$-alkoxy, R$^6$ stands for a $C_3$-$C_7$-cycloalkyl ring, whereby the ring has the above-indicated meaning, R$^7$ stands for $C_1$-$C_6$-alkyl, $C_2$-$C_6$-alkenyl, $C_2$-$C_6$-alkinyl, benzyl, $C_3$-$C_7$-cycloalkyl, with the above-indicated meaning, or for the group —NR$^3$R$^4$, or for $C_1$-$C_{10}$-alkyl, $C_2$-$C_{10}$-alkenyl, $C_2$-$C_{10}$-alkinyl or $C_3$-$C_7$-cycloalkyl that is substituted in one or more places in the same way or differently with hydroxy, $C_1$-$C_6$-alkoxy, halogen, phenyl, —NR$^3$R$^4$ or phenyl, which itself can be substituted in one or more places in the same way or differently with halogen, hydroxy, $C_1$-$C_6$-alkyl, $C_1$-$C_6$-alkoxy, halo-$C_1$-$C_6$-alkyl, or halo-$C_1$-$C_6$-alkoxy, or R$^7$ stands for phenyl, which itself can be substituted in one or more places in the same way or differently with halogen, hydroxy, $C_1$-$C_6$-alkyl or $C_1$-$C_6$-alkoxy, halo-$C_1$-$C_6$-alkyl, or halo-$C_1$-$C_6$-alkoxy, as well as isomers, diastereomers, enantiomers and salts thereof, are effective.

Compounds of general formula I$_f$, in which
Q stands for the group

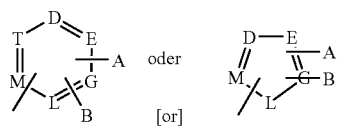

D, E, G,
L, M and T, in each case independently of one another, stand for carbon, oxygen, nitrogen or sulfur, whereby at least one heteroatom must be contained in the ring,
R$^1$ stands for halogen,
R$^2$ stands for $C_1$-$C_{10}$-alkyl that is substituted in one or more places in the same way or differently with hydroxy or $C_1$-$C_6$-alkyl,
X stands for the group —NH—,
A and B, in each case independently of one another, stand for hydrogen, halogen, or for the group —SR$^7$, —S(O) R$^7$, or —SO$_2$ R$^7$, R$^3$ and R$^4$ stand for hydrogen,
R$^7$ stands for $C_1$-$C_6$-alkyl, benzyl, or for the group —NR$^3$R$^4$,
as well as isomers, diastereomers, enantiomers and salts thereof, are especially effective.

The compounds according to the invention essentially inhibit cyclin-dependent kinases, upon which is based their action, for example, against cancer, such as solid tumors and leukemia; auto-immune diseases, such as psoriasis, alopecia, and multiple sclerosis, chemotherapy-induced alopecia and mucositis; cardiovascular diseases, such as stenoses, arterioscleroses and restenoses; infectious diseases, such as, e.g., by unicellular parasites, such as trypanosoma, toxoplasma or plasmodium, or produced by fungi; nephrological diseases, such as, e.g., glomerulonephritis, chronic neurodegenerative diseases, such as Huntington's disease, amyotropic lateral sclerosis, Parkinson's disease, AIDS, dementia and Alzheimer's disease; acute neurodegenerative diseases, such as ischemias of the brain and neurotraumas; viral infections, such as, e.g., cytomegalic infections, herpes, hepatitis B and C, and HIV diseases.

The eukaryotic cell division cycle ensures the duplication of the genome and its distribution to the daughter cells by passing through a coordinated and regulated sequence of events. The cell cycle is divided into four successive phases: the G1 phase represents the time before the DNA replication, in which the cell grows and is sensitive to external stimuli. In the S phase, the cell replicates its DNA, and in the G2 phase, preparations are made for entry into mitosis. In mitosis (M phase), the replicated DNA separates, and cell division is completed.

The cyclin-dependent kinases (CDKs), a family of serine/threonine kinases, whose members require the binding of a cyclin (Cyc) as a regulatory subunit in order for them to activate, drive the cell through the cell cycle. Different CDK/Cyc pairs are active in the various phases of the cell cycle. CDK/Cyc pairs that are important to the basic function of the cell cycle are, for example, CDK4(6)/CycD, CDK2/CycE, CDK2/CycA, CDK1/CycA and CDK1/CycB. Some members of the CDK enzyme family have a regulatory function by influencing the activity of the above-mentioned cell cycle CDKs, while no specific function could be associated with other members of the CDK enzyme family. One of the latter, CDK5, is distinguished in that it has an atypical regulatory subunit (p35) that deviates from the cyclins, and its activity is highest in the brain.

The entry into the cell cycle and the passage through the "restriction points," which marks the independence of a cell from further growth signals for the completion of the cell division that has begun, are controlled by the activity of the CDK4(6)/CycD and CDK2/CycE complexes. The essential substrate of these CDK complexes is the retinoblastoma protein (Rb), the product of the retinoblastoma tumor suppressor gene. Rb is a transcriptional co-repressor protein. In addition to other, still largely little understood mechanisms, Rb binds and inactivates transcription factors of the E2F type and forms transcriptional repressor complexes with histone-deacetylases (HDAC) (Zhang, H. S. et al. (2000). Exit from G1 and S Phase of the Cell Cycle is Regulated by Repressor Complexes Containing HDAC-Rb-hSWI/SNF and Rb-hSWI/SNF. *Cell* 101, 79-89). By the phosphorylation of Rb by CDKs, bonded E2F transcription factors are released and result in transcriptional activation of genes, whose products are required for the DNA synthesis and the progression through the S-phase. In addition, the Rb-phosphorylation brings about the breakdown of the Rb-HDAC complexes, by which additional genes are activated. The phosphorylation of Rb by CDKs is to be treated as equivalent to exceeding the "restriction points." For the progression through the S-phase and its completion, the activity of the CDK2/CycE and CDK2/CycA complexes is necessary, e.g., the activity of the transcription factors of the E2F type is turned off by means of phosphorylation by CDK2/CycA as soon as the cells are entered into the S-phase. After replication of DNA is complete, the CDK1 in the complex with CycA or CycB controls the entry into and the passage through phases G2 and M (FIG. 1).

According to the extraordinary importance of the cell-division cycle, the passage through the cycle is strictly regulated and controlled. The enzymes that are necessary for the progression through the cycle must be activated at the correct time and are also turned off again as soon as the corresponding phase is passed. Corresponding control points ("checkpoints") stop the progression through the cell cycle if DNA damage is detected, or the DNA replication or the creation of the spindle device is not yet completed.

The activity of the CDKs is controlled directly by various mechanisms, such as synthesis and degradation of cyclins, complexing of the CDKs with the corresponding cyclins, phosphorylation and dephosphorylation of regulatory threonine and tyrosine radicals, and the binding of natural inhibitory proteins. While the amount of protein of the CDKs in a proliferating cell is relatively constant, the amount of the individual cyclins oscillates with the passage through the cycle. Thus, for example, the expression of CycD during the early G1 phase is stimulated by growth factors, and the expression of CycE is induced after the "restriction points" are exceeded by the activation of the transcription factors of the E2F type. The cyclins themselves are degraded by the ubiquitin-mediated proteolysis. Activating and inactivating phosphorylations regulate the activities of the CDKs, for example phosphorylate CDK-activating kinases (CAKs) Thr160/161 of the CDK1, while, by contrast, the families of Wee1/Myt1 inactivate kinases CDK1 by phosphorylation of Thr14 and Tyr15. These inactivating phosphorylations can be destroyed in turn by cdc25 phosphatases. The regulation of the activity of the CDK/Cyc complexes by two families of natural CDK inhibitor proteins (CKIs), the protein products of the p21 gene family (p21, p27, p57) and the p16 gene family (p15, p16, p18, p19) is very significant. Members of the p21 family bind to cyclin complexes of CDKs 1,2,4,6, but inhibit only the complexes that contain CDK1 or CDK2. Members of the p16 family are specific inhibitors of the CDK4- and CDK6 complexes.

The plane of control point regulation lies above this complex direct regulation of the activity of the CDKs. Control points allow the cell to track the orderly sequence of the individual phases during the cell cycle. The most important control points lie at the transition from G1 to S and from G2 to M. The G1 control point ensures that the cell does not initiate any DNA synthesis unless it has proper nutrition, interacts correctly with other cells or the substrate, and its DNA is intact. The G2/M control point ensures the complete replication of DNA and the creation of the mitotic spindle before the cell enters into mitosis. The G1 control point is activated by the gene product of the p53 tumor suppressor gene. p53 is activated after detection of changes in metabolism or the genomic integrity of the cell and can trigger either a stopping of the cell cycle progression or apoptosis. In this case, the transcriptional activation of the expression of the CDK inhibitor protein p21 by p53 plays a decisive role. A second branch of the G1 control point comprises the activation of the ATM and Chk1 kinases after DNA damage by UV light or ionizing radiation and finally the phosphorylation and the subsequent proteolytic degradation of the cdc25A phosphatase (Mailand, N. et al. (2000). Rapid Destruction of Human cdc25A in Response to DNA Damage. *Science* 288, 1425-1429). A shutdown of the cell cycle results from this, since the inhibitory phosphorylation of the CDKs is not removed. After the G2/M control point is activated by damage of the DNA, both mechanisms are involved in a similar way in stopping the progression through the cell cycle.

The loss of the regulation of the cell cycle and the loss of function of the control points are characteristics of tumor cells. The CDK-Rb signal path is affected by mutations in over 90% of human tumor cells. These mutations, which finally result in inactivating phosphorylation of the RB, include the over-expression of D- and E-cyclins by gene amplification or chromosomal translocations, inactivating mutations or deletions of CDK inhibitors of the p16 type, as well as increased (p27) or reduced (CycD) protein degradation. The second group of genes, which are affected by mutations in tumor cells, codes for components of the control points. Thus p53, which is essential for the G1 and G2/M control points, is the most frequently mutated gene in human tumors (about 50%). In tumor cells that express p53 without mutation, it is often inactivated because of a greatly increased protein degradation. In a similar way, the genes of other proteins that are necessary for the function of the control points are affected by mutations, for example ATM (inactivating mutations) or cdc25 phosphatases (over-expression).

Convincing experimental data indicate that CDK2/Cyc complexes occupy a decisive position during the cell cycle progression: (1) Both dominant-negative forms of CDK2, such as the transcriptional repression of the CDK2 expression by anti-sense oligonucleotides, produce a stopping of the cell cycle progression. (2) The inactivation of the CycA gene in mice is lethal. (3) The disruption of the function of the CDK2/CycA complex in cells by means of cell-permeable peptides resulted in tumor cell-selective apoptosis (Chen, Y. N. P. et al. (1999). Selective Killing of Transformed Cells by Cyclin/Cyclin-Dependent Kinase 2 Antagonists. *Proc. Natl. Acad. Sci. USA* 96, 4325-4329).

Changes of the cell cycle control play a role not only in carcinoses. The cell cycle is activated by a number of viruses, both by transforming viruses as well as by non-transforming viruses, to make possible the replication of viruses in the host cell. The false entry into the cell cycle of normally post-mitotic cells is associated with various neurodegenerative diseases. The mechanisms of the cell cycle regulation, their changes in diseases and a number of approaches to develop inhibitors of the cell cycle progression and especially the CDKs were already described in a detailed summary in several publications (Sielecki, T. M. et al. (2000). Cyclin-Dependent Kinase Inhibitors: Useful Targets in Cell Cycle Regulation. *J. Med. Chem.* 43, 1-18; Fry, D. W. & Garrett, M. D. (2000). Inhibitors of Cyclin-Dependent Kinases as Therapeutic Agents for the Treatment of Cancer. *Curr. Opin. Oncol. Endo. Metab. Invest. Drugs* 2, 40-59; Rosiania, G. R. & Chang, Y. T. (2000). Targeting Hyperproliferative Disorders with Cyclin-Dependent Kinase Inhibitors. *Exp. Opin. Ther. Patents* 10, 215-230; Meijer, L. et al. (1999). Properties and Potential Applications of Chemical Inhibitors of Cyclin-Dependent Kinases.

Pharmacol. Ther. 82, 279-284; Senderowicz, A. M. & Sausville, E. A. (2000). Preclinical and Clinical Development of Cyclin-Dependent Kinase Modulators. *J. Natl. Cancer Inst.* 92, 376-387).

To use the compounds according to the invention as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers; salts for changing the osmotic pressure or buffers. These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants, such as salts of bile acids or animal or plant phospholipids, but also mixtures thereof, as well as liposomes or their components can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into two or more daily doses.

Subjects of this invention also include the use of compounds of general formula I or $I_f$ for the production of a pharmaceutical agent for treating cancer, auto-immune diseases, cardiovascular diseases, chemotherapy agent-induced alopecia and mucositis, infectious diseases, nephrological diseases, chronic and acute neurodegenerative diseases and viral infections, whereby cancer is defined as solid tumors and leukemia; auto-immune diseases are defined as psoriasis, alopecia and multiple sclerosis; cardiovascular diseases are defined as stenoses, arterioscleroses and restenoses; infectious diseases are defined as diseases that are caused by unicellular parasites; nephrological diseases are defined as glomerulonephritis; chronic neurodegenerative diseases are defined as Huntington's disease, amyotrophic lateral sclerosis, Parkinson's disease, AIDS, dementia and Alzheimer's disease; acute neurodegenerative diseases are defined as ischemias of the brain and neurotraumas; and viral infections are defined as cytomegalic infections, herpes, hepatitis B or C, and HIV diseases.

Subjects of this invention also include pharmaceutical agents for treating the above-cited diseases, which contain at least one compound according to general formula I or $I_f$, as well as pharmaceutical agents with suitable formulation substances and vehicles.

The compounds of general formula I or $I_f$ according to the invention are, i.a., excellent inhibitors of the cyclin-dependent kinases, such as CDK1, CDK2, CDK3, CDK4, CDK5, CDK6, CDK7, CDK8 and CDK9, as well as the glycogen-synthase-kinase (GSK-3β).

If the production of the starting compounds is not described, the latter are known or can be produced analogously to known compounds or to processes that are described here. It is also possible to perform all reactions that are described here in parallel reactors or by means of combinatory operating procedures.

The isomer mixtures can be separated into the enantiomers or E/Z isomers according to commonly used methods, such as, for example, crystallization, chromatography or salt formation.

The production of the salts is carried out in the usual way by a solution of the compound of formula I or $I_f$ being mixed with the equivalent amount of or excess base or acid, which optionally is in solution, and the precipitate being separated or the solution being worked up in the usual way.

Production of the Compounds According to the Invention

The following examples explain the production of the compounds according to the invention, without the scope of the claimed compounds being limited to these examples.

The compounds of general formula I of $I_f$ according to the invention can be produced according to the following diagrams of the process 1-6:

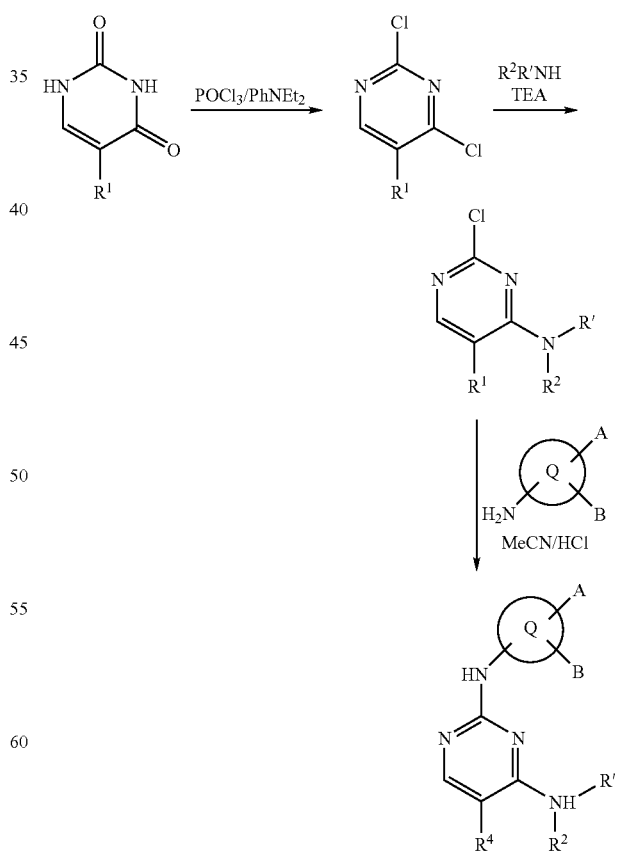

in which the substituents R1, R2 and

19

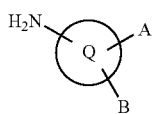

are defined according to formula I, and B
R¹ stands for C1-C3-alkyl in keeping with formula I.

Diagram 1.2

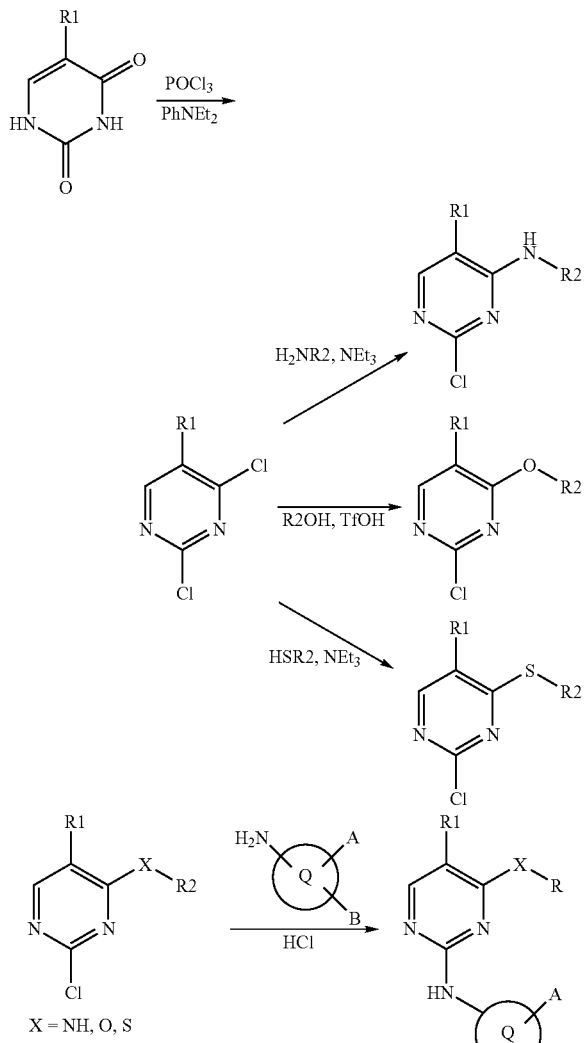

in which the indicated substituents are defined according to formula I, whereby X does not stand for —N(C1-C6-alkyl)-.

Figure 1:
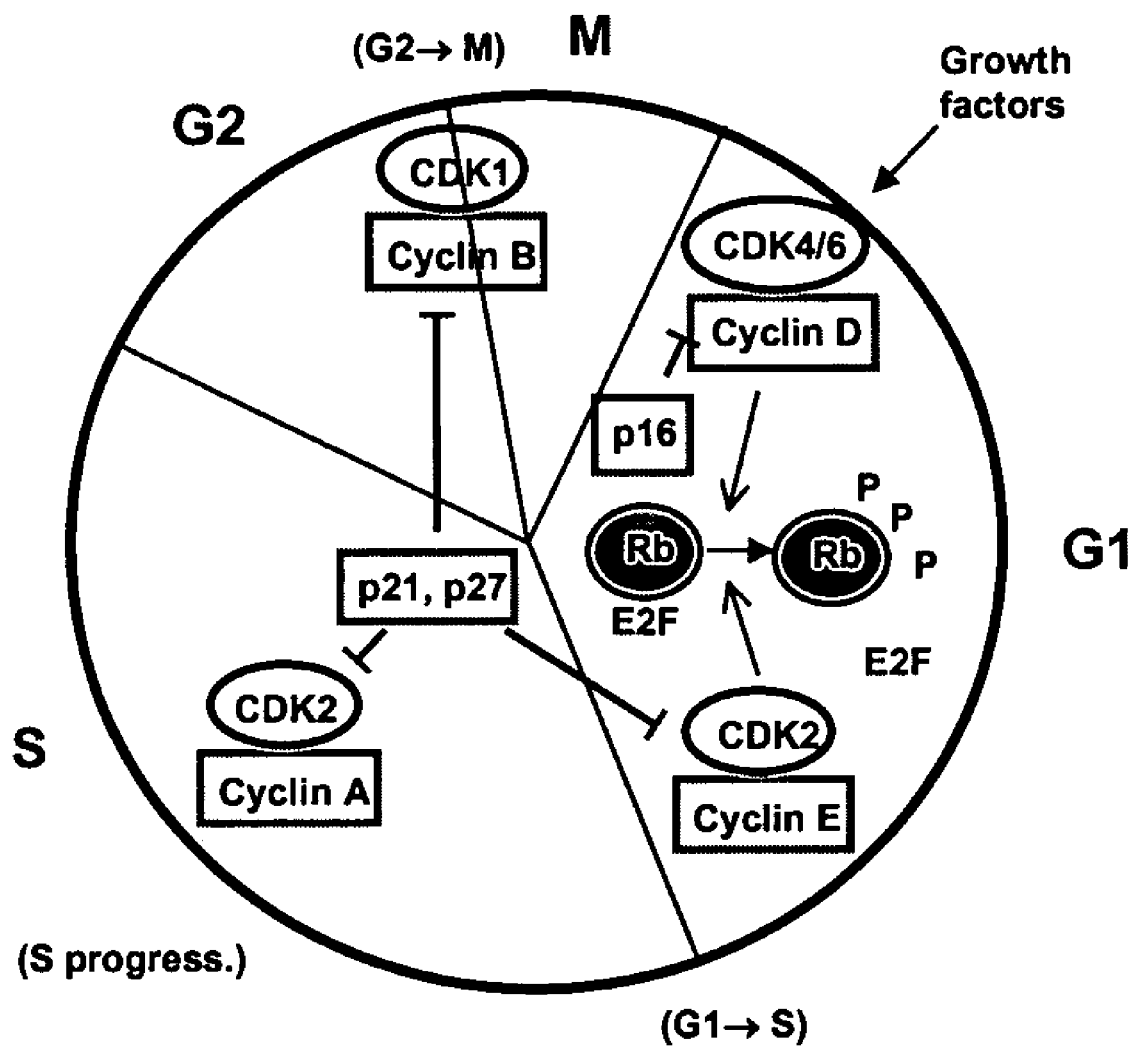
FIG. 1 illustrates a cell cycle.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1.0

Production of 5-[5-bromo-4-(cyclopropylmethyl-amino)-pyrimidin-2-ylamino]-pyridine-2-sulfonic acid amide

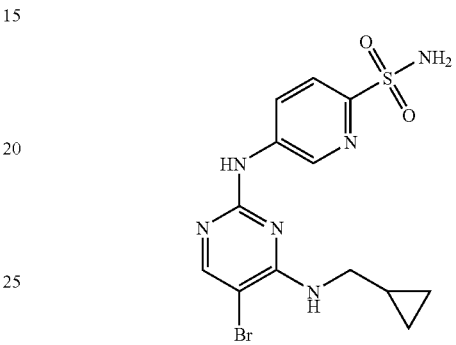

263 mg (1.0 mmol) of (5-bromo-2-chloro-pyrimidin-4-yl)-cyclopropylmethyl-amine is dissolved in 2 ml of acetonitrile and added to a suspension of 172 mg (1.0 mmol) of 5-amino-pyridine-2-sulfonic acid amide (representation according to W. T. Caldwell, E. C. Kornfeld *J. Am. Chem. Soc.* 1942, 64, 1695-1698) in 1 ml of acetonitrile, 0.25 ml of a 4 molar solution of hydrochloric acid in 1,4-dioxane as well as 0.25 ml of water. The reaction mixture is stirred under reflux overnight. After cooling, the precipitate that is formed is filtered off and washed with warm water. After drying, 286 mg (0.72 mmol, 72% of theory) of the product 5-[5-bromo-4-(cyclopropylmethyl-amino)-pyrimidin-2-ylamino]-pyridine-2-sulfonic acid amide is obtained.

¹H-NMR: 10.79 (s, 1H), 8.96 (d, 1H), 8.25 (m, 3H), 7.88 (d, 1H), 7.39 (br, 2H), 3.32 (m, 2H), 1.17 (m, 1H), 0.45 (m, 2H), 0.33 (m, 2H).

MS: 398 (EI).

EXAMPLE 1.1

(R)-2-[5-Bromo-2-(5-methylsulfanyl-4H-[1,2,4]tria-zol-3-ylamino)-pyrimidin-4-ylamino]-3-methyl-butan-1-ol 117 mg (0.9 mmol) of 5-methylsulfanyl-4H-[1,2,4]tria-zol-3-ylamine is dissolved in 3 ml of acetonitrile as well as 0.20 ml of water. While being stirred, it is mixed with 0.23 ml of a 4 molar solution of hydrochloric acid in 1,4-dioxane. After 5 minutes, 294 mg (1 mmol) of (R)-2-(5-bromo-2-chloro-pyrimidin-4-ylamino)-3-methyl-butan-1-ol is added, and the reaction mixture is stirred for 142 hours at 70° C. After cooling, the batch is purified by chromatography (methylene chloride-(methylene chloride/ethanol: 9/1); Flashmaster II).

56 mg (0.14 mmol, 16% of theory) of the product (R)-2-[5-bromo-2-(5-methylsulfanyl-4H-[1,2,4]triazol-3-ylamino)-pyrimidin-4-ylamino]-3-methyl-butan-1-ol is obtained.

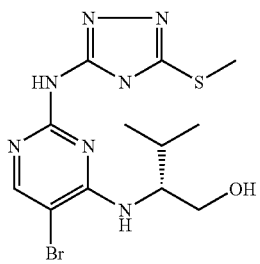

¹H-NMR: 8.30 (s,1H), 7.61 (s,2H), 6.82 (d,1H), 4.87 (t,1H), 3.92 (br,1H), 3.62 (dd,2H), 2.48 (s,3H), 1.98 (m,1H), 0.96 (d,3H), 0.88 (d,3H).
MS: 388 (EI)

EXAMPLE 1.2

(R)-2-[5-Bromo-2-(5-methanesulfinyl-4H-[1,2,4]triazol-3-ylamino)pyrimidin-4-ylamino]-3-methyl-butan-1-ol At 0° C., 159 mg (0.41 mmol) of (R)-2-[5-bromo-2-(5-methylsulfanyl-4H-[1,2,4]triazol-3-ylamino)-pyrimidin-4-ylamino]-3-methyl-butan-1-ol in 4 ml of MeOH/water (4:1) is mixed with 80 mg (0.95 mmol) of $NaHCO_3$ and 98 mg (0.95 mmol) of oxone. The reaction mixture is stirred for 2 hours at room temperature, then another 50 mg (0.5 mmol) of oxone is added, and it is stirred for 1 hour at 30° C. The batch is diluted with water and extracted with ethyl acetate. The organic phase is concentrated by evaporation and purified by chromatography (methylene chloride-(methylene chloride/ethanol: 9/1); Flashmaster II). After the recrystallization, 45 mg (0.11 mmol, 27% of theory) of the product (R)-2-[5-bromo-2-(5-methanesulfinyl-4H-[1,2,4]triazol-3-ylamino)-pyrimidin-4-ylamino]-3-methyl-butan-1-ol is obtained.

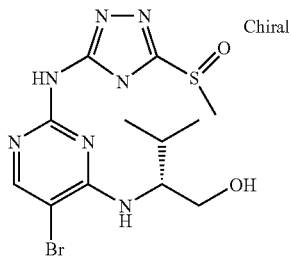

¹H-NMR: 8.38 (s,1H), 7.90 (s,2H), 6.99 (d,1H), 4.87 (t,1H), 3.95 (m,1H), 3.62 (dd,2H), 2.90 (s,3H), 2.00 (m,1H), 0.96 (d,3H), 0.88 (d,3H).
MS: 404 (ES)

EXAMPLE 1.3

(R)-2-[5-Bromo-2-(5-methanesulfonyl-4H-[1,2,4]triazol-3-ylamino)-pyrimidin-4-ylamino]-3-methyl-butan-1-ol 35 mg (0.086 mmol) of (R)-2-[5-bromo-2-(5-methanesulfinyl-4H-[1,2,4]triazol-3-ylamino)-pyrimidin-4-ylamino]-3-methyl-butan-1-ol is dissolved in 4 ml of MeOH/water (4:1) and stirred with 25 mg of oxone (0.25 mmol) at room temperature. The batch is diluted with water and extracted with ethyl acetate. The organic phase is concentrated by evaporation, and the residue is digested with ethyl acetate. 19 mg (0.045 mmol, 52% of theory) of the product (R)-2-[5-bromo-2-(5-methanesulfonyl-4H-[1,2,4]triazol-3-ylamino)-pyrimidin-4-ylamino]-3-methyl-butan-1-ol is obtained.

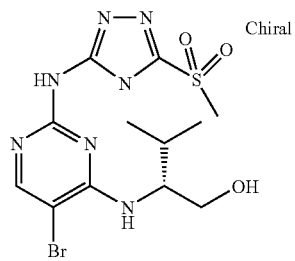

¹H-NMR: 8.39 (s, 1H), 7.95 (s, 2H), 7.02 (d,1H), 4.87 (t, 1H), 3.96 (m, 1H), 3.62 (dd, 2H), 3.30 (s, 3H), 2.00 (m, 1H), 0.96 (d, 3H), 0.88 (d, 3H).
MS: 420 (ES)

EXAMPLE 1.4

Production of 5-[5-Bromo-4-(4-hydroxy-butylsulfanyl)-pyrimidin-2-ylamino]-pyridine-2-sulfonic acid amide

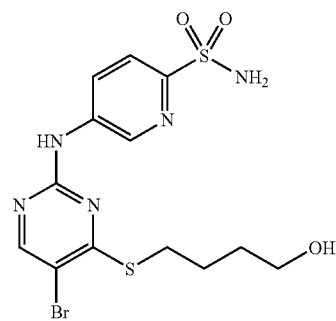

298 mg (1.0 mmol) of 4-(5-bromo-2-chloro-pyrimidin-4-ylsulfanyl)-butan-1-ol is dissolved in 2 ml of acetonitrile and added to a suspension of 172 mg (1.0 mmol) of 5-amino-pyridine-2-sulfonic acid amide (representation according to W. T. Caldwell, E. C. Kornfeld *J Am. Chem. Soc.* 1942, 64, 1695-1698) in 1 ml of acetonitrile, 0.25 ml of a 4 molar solution of hydrochloric acid in 1,4-dioxane as well as 0.25 ml of water. The reaction mixture is stirred under reflux for 24 hours. It is mixed with 1 ml of ethanol and stirred for another 24 hours under reflux. After cooling, the precipitate that is formed is filtered off, and the filtrate is concentrated by evaporation. The residue is purified by chromatography (Flashmaster II, DCM/MeOH 9:1). The crude product that is obtained is then purified by preoperative thin-layer chromatography. 43 mg (0.10 mmol, 10% of theory) of the product 5-[5-bromo-4-(4-hydroxy-butylsulfanyl)-pyrimidin-2-ylamino]-pyridine-2-sulfonic acid amide is obtained ¹H-NMR: 10.38 (s,1H), 8.93 (d, 1H), 8.38 (m, 2H), 7.82 (m, 3H), 3.42 (t, 2H), 3.33 (t, 2H), 1.75 (m, 2H), 1.54 (m, 2H).

MS: 434 (ES).

EXAMPLE 1.5

Production of (R)-4-[5-bromo-4-(1-hydroxymethyl-propylamino)-pyrimidin-2-ylamino]-thiophene-2-sulfonic acid amide

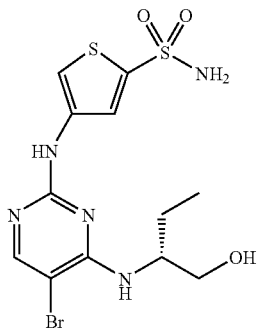

530 mg (1.9 mmol) of (R)-2-(5-bromo-2-chloro-pyrimidin-4-ylamino)-butan-1-ol is added to a suspension of 303 mg of a mixture that consists of 4-amino-thiophene-2-sulfonic acid amide and 5-amino-thiophene-2-sulfonic acid amide (ratio: 2:1) in 7 ml of ethanol and 170 µl of concentrated HCl. The reaction mixture is stirred for 21 hours under reflux. After cooling, the batch is purified by chromatography (Flashmaster II, hexane/EE 2:8). The crude product that is obtained is then recrystallized (ethyl acetate/diisopropyl ether). 47 mg (0.11 mmol, 7% of theory) of the product 4-[5-bromo-4-(1-hydroxymethyl-propylamino)-pyrimidin-2-ylamino]-thiophene-2-sulfonic acid amide is obtained.

¹H-NMR: 9.75 (s, 1H), 8.05 (s, 1H), 7.65 (m, 4H), 6.28 (d, 1H), 4.88 (t, 1H), 4.04 (m, 1H), 3.55 (m, 2H), 1.62 (m, 2H), 0.90 (t, 3H).

MS: 422 (ES).

In a method similar to Diagrams 1.1 and 1.2 and the above-mentioned examples, the compounds below were also produced.

All NMR spectra are measured in the indicated solvent or in DMSO.

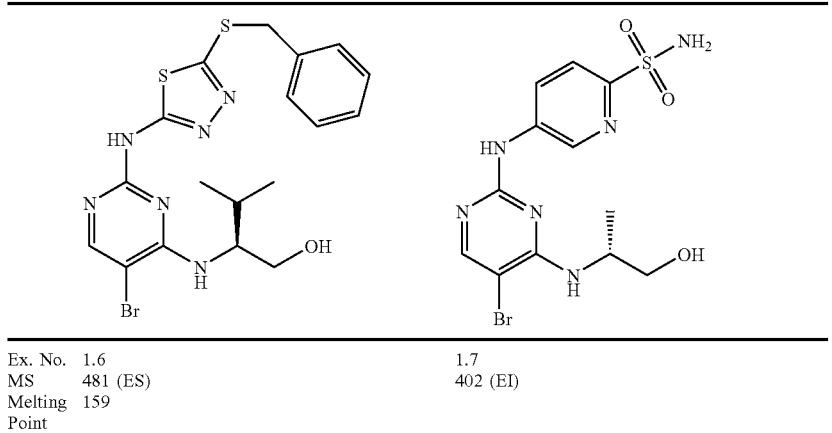

| Ex. No. | 1.6 | 1.7 |
|---|---|---|
| MS | 481 (ES) | 402 (EI) |
| Melting Point | 159 | |

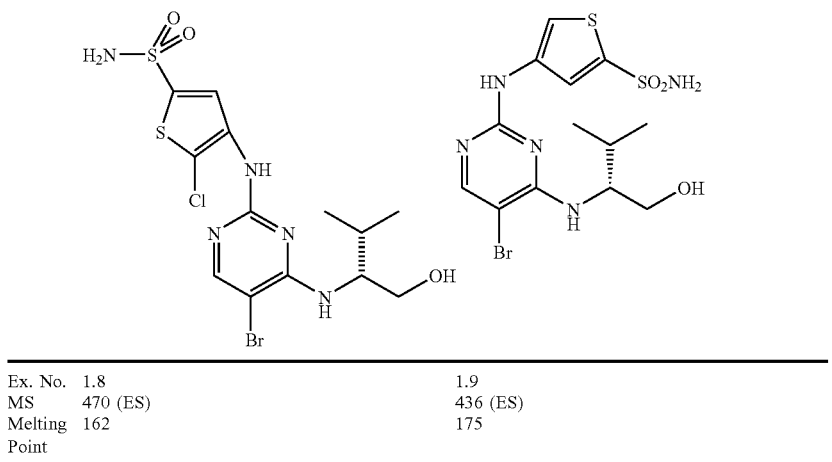

| Ex. No. | 1.8 | 1.9 |
|---|---|---|
| MS | 470 (ES) | 436 (ES) |
| Melting Point | 162 | 175 |

-continued
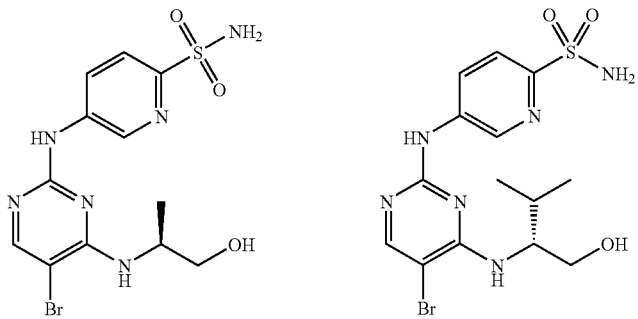
| Ex. No. | 1.10 | 1.11 |
|---|---|---|
| MS | 403 (ES) | 432 (EI) |
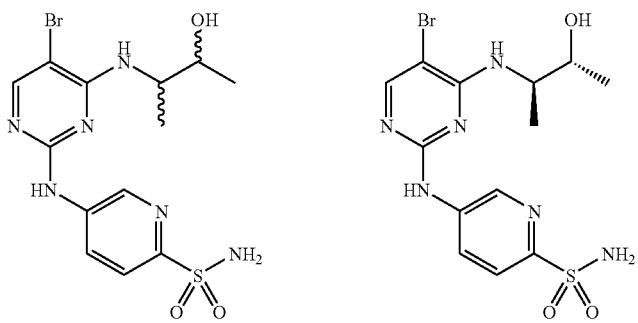
| Ex. No. | 1.12 | 1.13 |
|---|---|---|
| MS | ESI: | ESI: |
| | 417 (48%, M+) | 417 (96%, M+) |
| | 282 (42%) | |
| | 170 (100%) | |
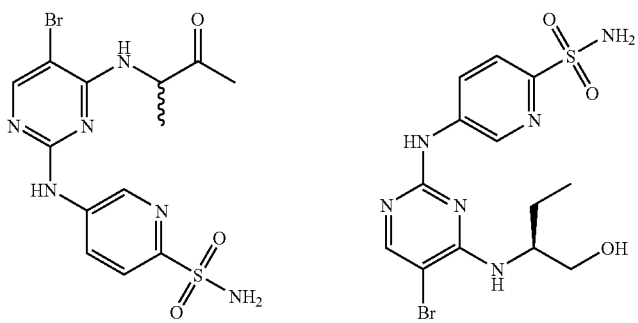
| Ex. No. | 1.14 | 1.15 |
|---|---|---|
| MS | 417 (99%, MH+) | 416 (EI) |
| | 415 (92%) | |
| | 115 (13%) | |

-continued
| | |
|---|---|
| 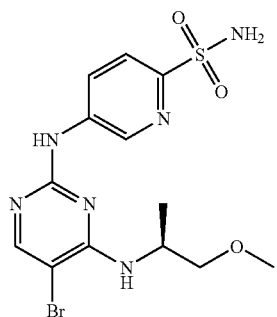 | 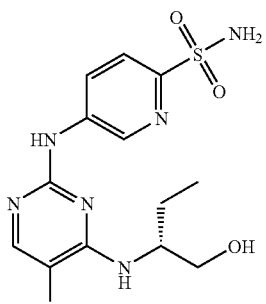 |
| Ex. No. 1.16<br>MS 416 (EI) | 1.17<br>416 (EI) |
| 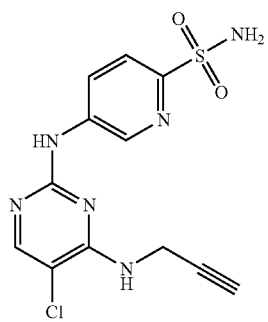 | 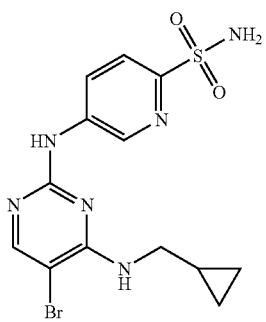 |
| Ex. No. 1.18<br>MS 337 (EI) | 1.19<br>398 (EI) |
| 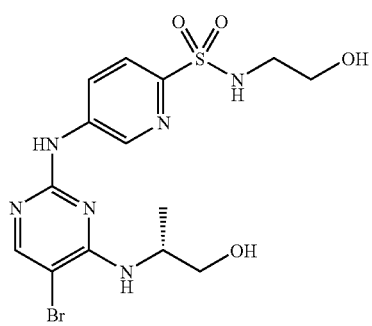 | 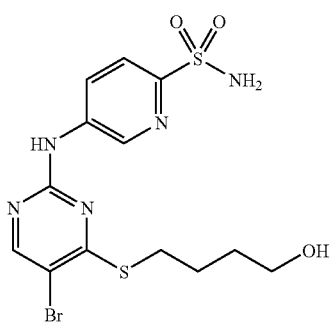 |
| Ex. No. 1.20<br>MS 447 (ES) | 1.21<br>434 (ES) |
| 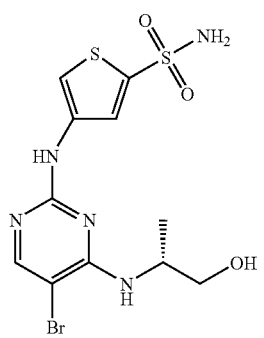 | 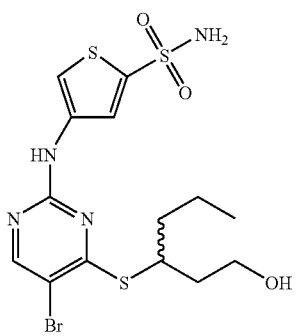 |
| Ex. No. 1.22<br>MS 408 (ES) | 1.23<br>467 (ES) |

| | |
|---|---|
| 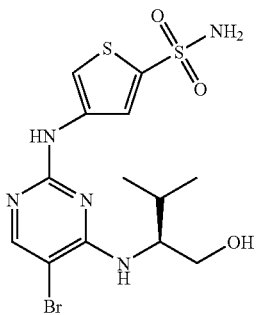 | 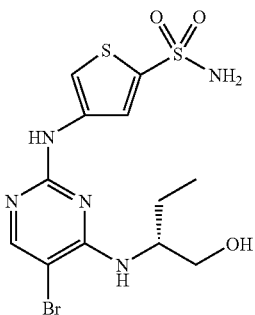 |
| Ex. No. 1.24<br>MS 436 (ES) | 1.25<br>422 (ES) |

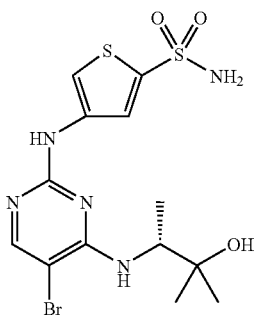

Ex. No. 1.26
MS 436 (ES)

EXAMPLE 1.27

Production of threo-4-[5-bromo-4-(2-hydroxy-1-methyl-propylamino)-pyrimidin-2-ylamino]-thiophene-2-sulfonic acid amide (according to Diagram 1.1 or 1.2):

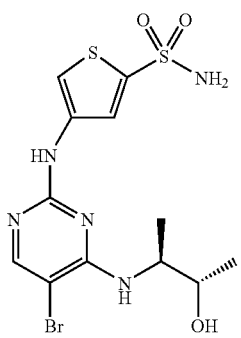

250 mg (0.9 mmol) of threo-3-(5-bromo-2-chloro-pyrimidin-4-ylamino)-butan-2-ol is added to a reaction mixture of 239 mg (1.34 mmol) of 4-amino-thiophene-2-sulfonic acid amide and 0.38 ml of a 4 molar solution of hydrochloric acid in 1,4-dioxane as well as 5 ml of acetonitrile and 0.2 ml of water.

The reaction mixture is stirred under reflux for 23 hours. After cooling, the solid that is formed is suctioned off and washed with ethanol and water. The filtrate is concentrated by evaporation, and the residue that is obtained is purified by chromatography (Flashmaster II, DCM/EtOH 9:1). A total of 290 mg (0.69 mmol, 77% of theory) of the product threo-4-[5-bromo-4-(2-hydroxy-1-methyl-propylamino)-pyrimidin-2-ylamino]-thiophene-2-sulfonic acid amide is obtained.

$^1$H-NMR: 10.90 (s, 1H), 8.23 (s, 1H), 7.70 (m, 4H), 7.21 (br,1H), 4.13 (m, 1H), 3.81 (m, 1H), 1.25 (d, 3H), 1.10 (d, 3H).

MS: 422 (ES).

Diagram 2: Synthesis with Use of Thiophene-Sulfonyl Fluorides

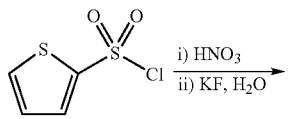 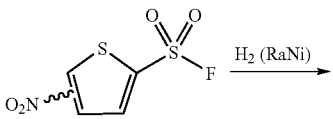 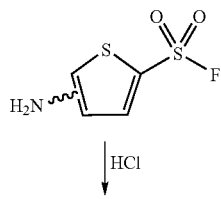

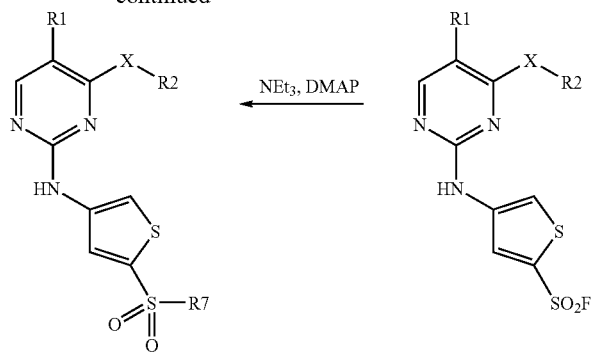

EXAMPLE 2.0

Production of (R)₄-[5-bromo-4-(2-hydroxy-1-methyl-ethylamino)-pyrimidin-2-ylamino]-thiophene-2-sulfonic acid-cyclopropylmethyl-amide according to Diagram 2

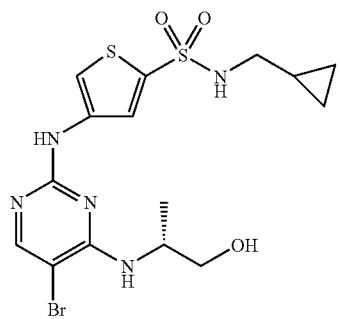

A reaction mixture of 130 mg (0.31 mmol) of (R)-4-[5-bromo-4-(2-hydroxy-1-methyl-ethylamino)-pyrimidin-2-ylamino]-thiophene-2-sulfonyl fluoride, 22 mg (0.31 mg) of aminomethylcyclopropane, 43 µl (0.31 mmol) of triethylamine as well as 38 mg (0.31 mmol) of DMAP in 2-butanol is stirred under reflux for 43 hours. It is mixed again with 22 mg (0.31 mg) of aminomethylcyclopropane, 43 µl (0.31 mmol) of triethylamine as well as 38 mg (0.31 mmol) of DMAP and stirred for another 24 hours under reflux. After cooling, the batch is purified by chromatography (Flashmaster II, DCM/ethanol 95:5), and the crude product that is obtained is recrystallized (ethanol/diisopropyl ether). 35 mg (0.08 mmol, 26% of theory) of the product 4-[5-bromo-4-(2-hydroxy-1-methyl-ethylamino)-pyrimidin-2-ylamino]-thiophene-2-sulfonic acid cyclopropylmethyl-amide is obtained.

$^1$H-NMR: 9.86 (s, 1H), 8.05 (s, 1H), 7.94 (t, 1H), 7.71 (d, 1H), 7.63 (d, 1H), 6.33 (d, 1H), 4.91 (t, 1H), 4.20 (m, 1H), 3.49 (1,2H), 2.72 (t, 2H), 1.20 (d, 3H), 0.85 (m, 1H), 0.41 (m, 2H), 0.15 (m, 2H).

MS: 462 (ES).

The compounds below were also produced in a way similar to Diagram 2 and the above-mentioned example.

All NMR spectra are measured in the indicated solvent or in DMSO.

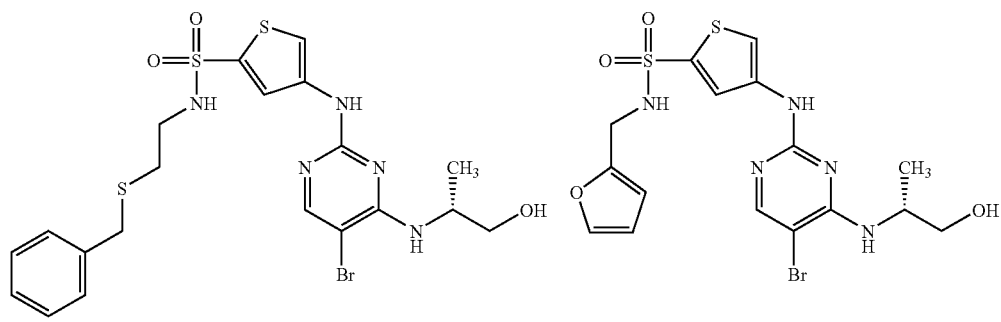

| Ex. No. | 2.1 | 2.2 |
|---|---|---|
| MS | 558 (ES) | 488 (ES) |

-continued
| | |
|---|---|
| 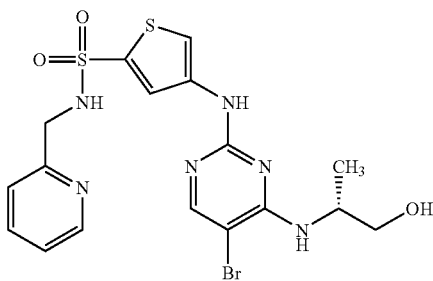 | 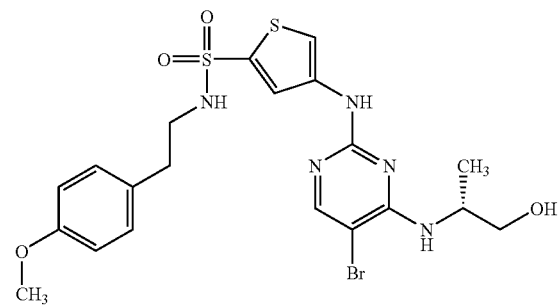 |
| Ex. No. 2.3 | 2.4 |
| MS 499 (ES) | 542 (ES) |
| 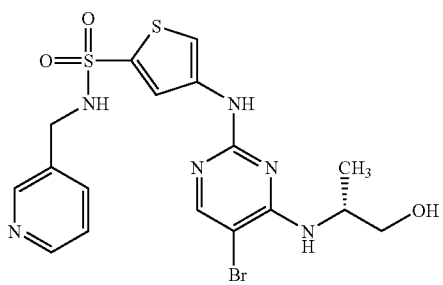 | 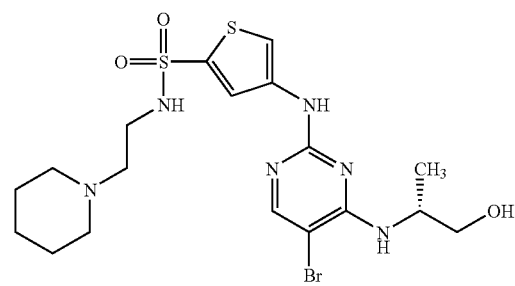 |
| Ex. No. 2.5 | 2.6 |
| MS 499 (ES) | 519 (ES) |
| 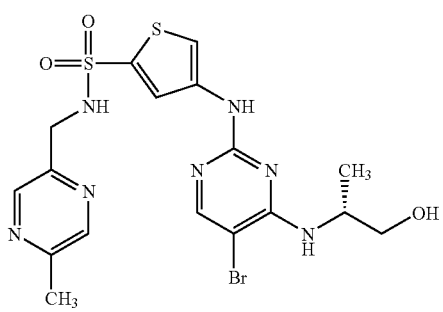 | 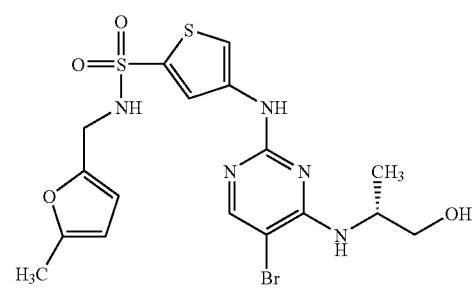 |
| Ex. No. 2.7 | 2.8 |
| MS 514 (ES) | 502 (ES) |
| 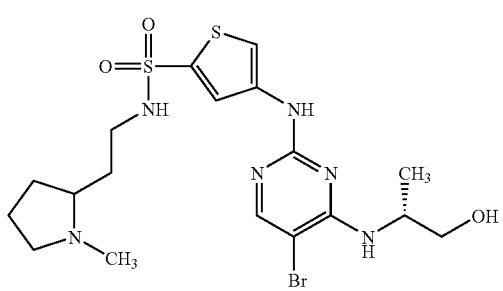 | 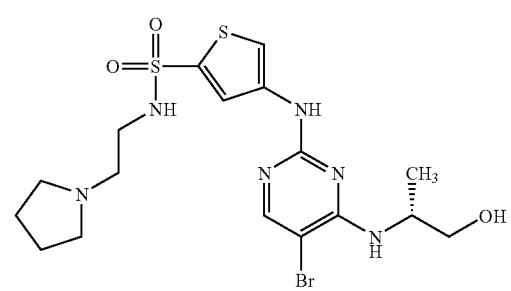 |
| Ex. No. 2.9 | 2.10 |
| MS 519 (ES) | 505 (ES) |

-continued
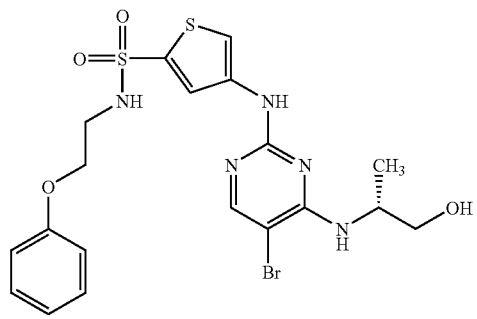 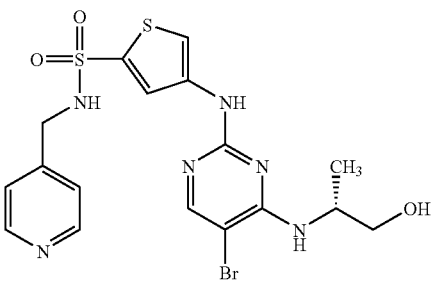
| Ex. No. | 2.11 | 2.12 |
| --- | --- | --- |
| MS | 528 (ES) | 499 (ES) |
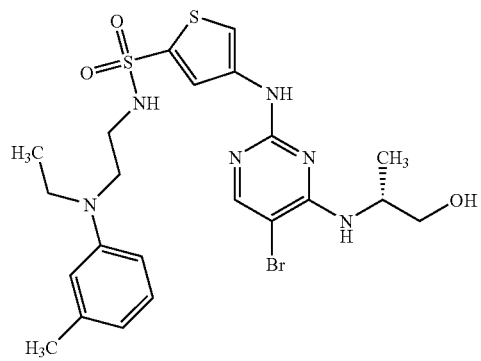 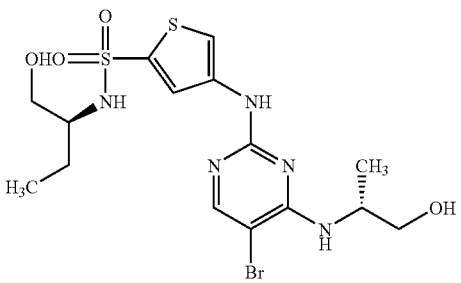
| Ex. No. | 2.13 | 2.14 |
| --- | --- | --- |
| MS | 569 (ES) | 480 (ES) |
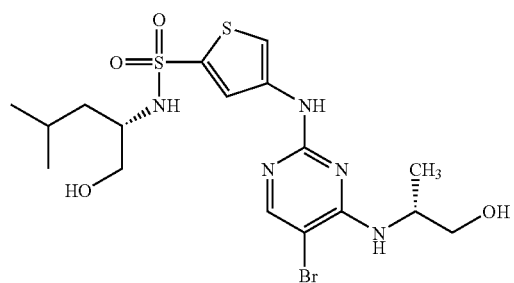 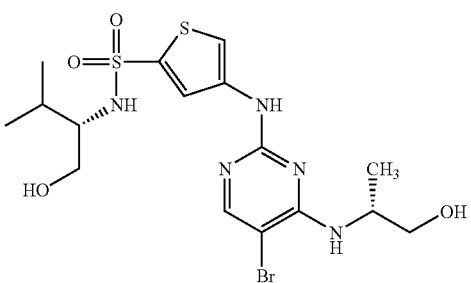
| Ex. No. | 2.15 | 2.16 |
| --- | --- | --- |
| MS | 508 (ES) | 494 (ES) |
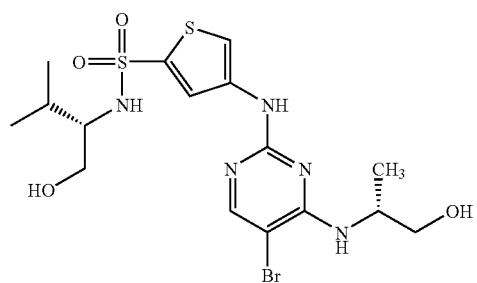 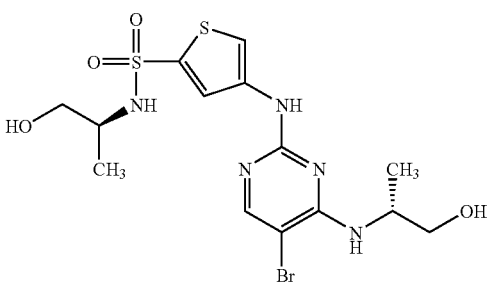
| Ex. No. | 2.17 | 2.18 |

| | |
|---|---|
| MS 494 (ES) | 466 (ES) |
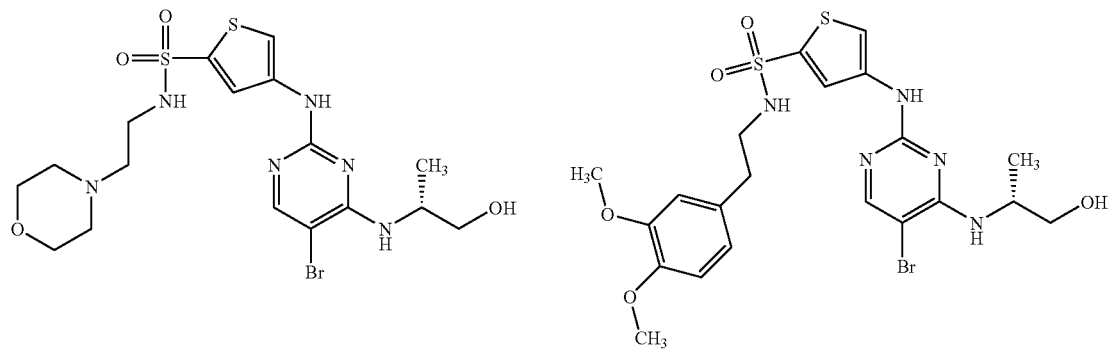
| | | | |
|---|---|---|---|
| Ex. No. | 2.19 | | 2.20 |
| MS | 558 (ES) | | 572 (ES) |
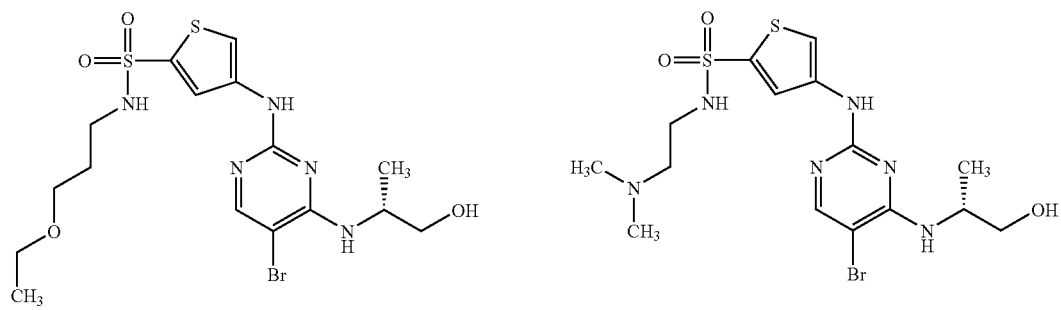
| | | | |
|---|---|---|---|
| Ex. No. | 2.21 | | 2.22 |
| MS | 494 (ES) | | 479 (ES) |
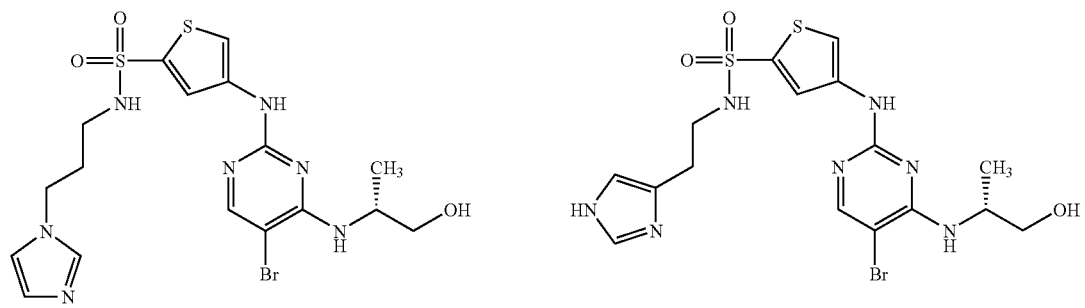
| | | | |
|---|---|---|---|
| Ex. No. | 2.23 | | 2.24 |
| MS | 516 (ES) | | 502 (ES) |

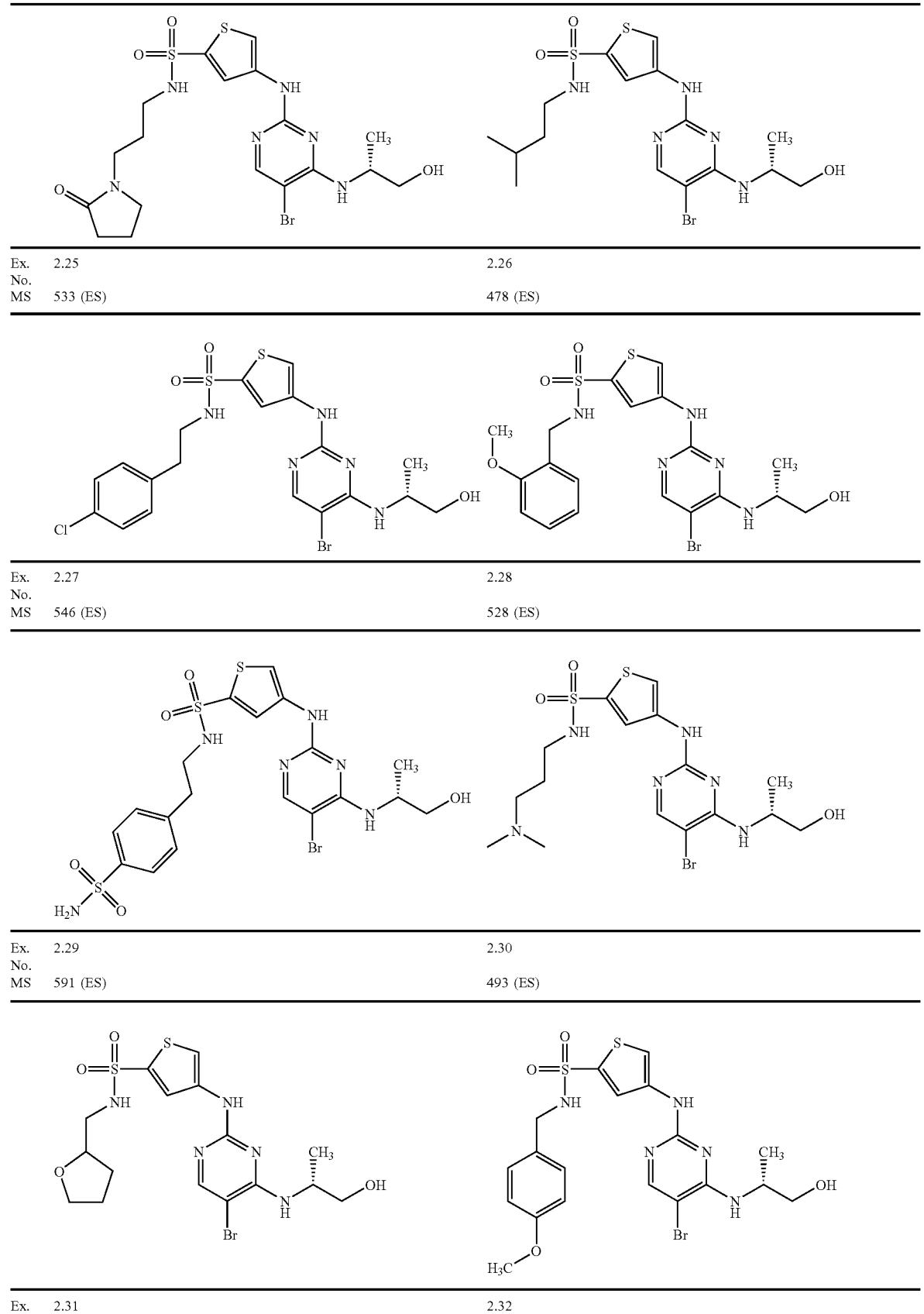
| Ex. No. | 2.25 | 2.26 |
|---|---|---|
| MS | 533 (ES) | 478 (ES) |
| Ex. No. | 2.27 | 2.28 |
|---|---|---|
| MS | 546 (ES) | 528 (ES) |
| Ex. No. | 2.29 | 2.30 |
|---|---|---|
| MS | 591 (ES) | 493 (ES) |
| Ex. | 2.31 | 2.32 |

-continued

| No. | | |
|---|---|---|
| MS | 492 (ES) | 528 (ES) |

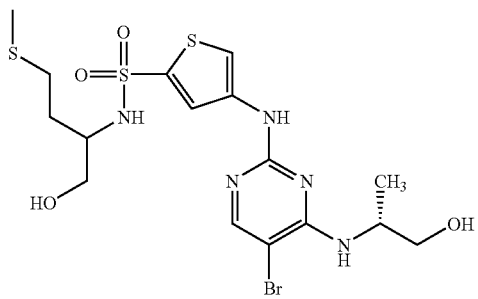 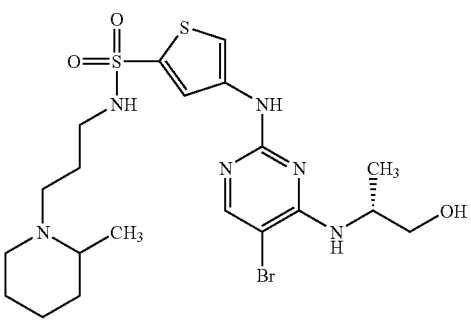

| Ex. No. | 2.33 | 2.34 |
|---|---|---|
| MS | 526 (ES) | 547 (ES) |

Diagram 3:

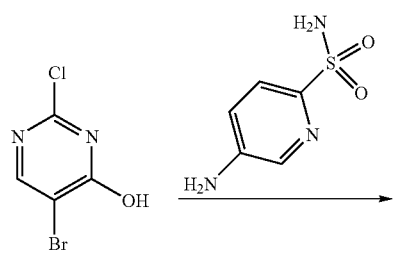

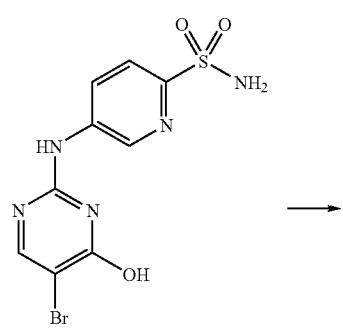

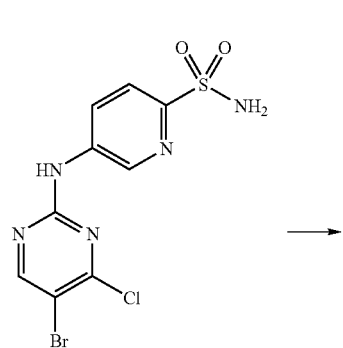

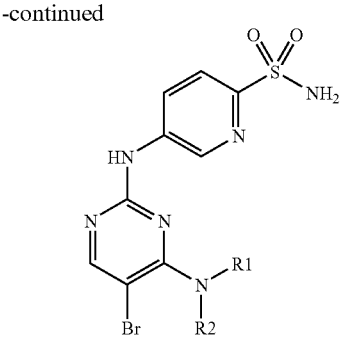

The compounds below are produced according to at least one process step from Diagram 3.

EXAMPLE 3.0

Production of 5-(5-Bromo-4-hydroxy-pyrimidin-2-ylamino)-pyridine-2-sulfonic acid amide 2.0 g (9.62 mmol) of 5-bromo-2-chloro-4-hydroxypyrimidine and 1.686 g (9.62 mmol) of 5-amino-pyridine-2-sulfonic acid amide are mixed in 50 ml of DMF (p.a.) with 2.88 ml of hydrochloric acid (4 molar in dioxane). It is stirred for 30 hours at 100° C., cooled and concentrated by evaporation. After being taken up in methanol, 1.505 g (45% of theory) of 5-(5-bromo-4-hydroxy-pyrimidin-2-ylamino)-pyridine-2-sulfonic acid amide is crystallized out, which is dried at 50° C. in a vacuum.

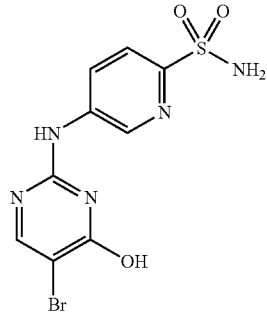

MS (ESI): 346 (94%, M$^+$), 268 (32%)

EXAMPLE 3.1

Production of 5-(5-bromo-4-chloro-pyrimidin-2-ylamino)-pyridine-2-sulfonic acid amide 175 mg (0.5 mmol) of 5-(5-bromo-4-hydroxy-pyrimidin-2-ylamino)-pyridine-2-sulfonic acid amide is refluxed with 20 mg of N,N-diethylaniline in 2 ml of phosphorus oxychloride for 3 hours. Then, it is cooled, poured onto ice and stirred for 30 minutes. The precipitated crystals are suctioned off, washed with water and acetonitrile and dried at 50° C. in a vacuum. Yield: 155 mg (85% of theory) of 5-(5-bromo-4-chloro-pyrimidin-2-ylamino)-pyridine-2-sulfonic acid amide.

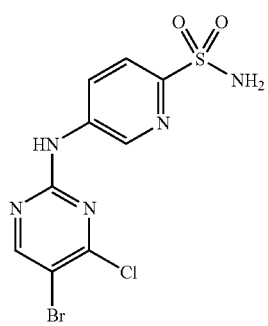

MS (ESI): 364 (20%, M+), 221 (48%), 150 (100%)

EXAMPLE 3.2

Production of 5-{5-bromo-4-[(2-hydroxy-1-methyl-propyl)-methyl-amino]-pyrimidin-2-ylamino}-pyridine-2-sulfonic acid amide 45 mg of 0.123 mg (0.123 mmol) of 5-(5-bromo-4-chloro-pyrimidin-2-ylamino)-pyridine-2-sulfonic acid amide is dissolved in 2.5 ml of DMF p.a. with 3 equivalents of the corresponding amine threo-3-methylamino-butan-2-ol that is stirred for 4 hours at 50° C. Concentration by evaporation, uptake in methanol and crystals being suctioned off or flash (dichloromethane/MeOH 9:1) yield 39.5 mg of 5-{5-bromo-4-[(2-hydroxy-1-methyl-propyl)-methyl-amino]-pyrimidin-2-ylamino}-pyridine-2-sulfonic acid amide (75% of theory).

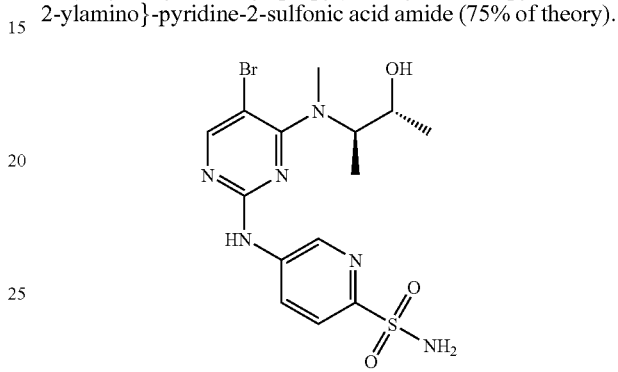

MS (ESI): 431 (38%, M+), 387(26%), 120 (100%)

The compounds below were produced in a way similar to Diagram 3 and the corresponding examples.

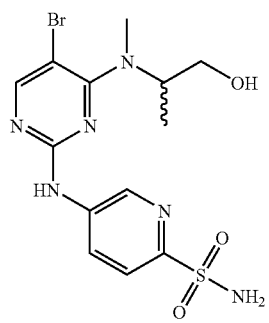

| Ex. No. | 3.3 | 3.4 |
|---|---|---|
| MS | ESI: | EI: |
| | M+ 417 (48%) | MH+: 433 (100%) |
| | 282 (42%) | 431 (95%) |
| | 170 (100%) | 243 (32%) |

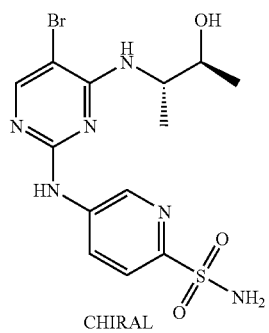 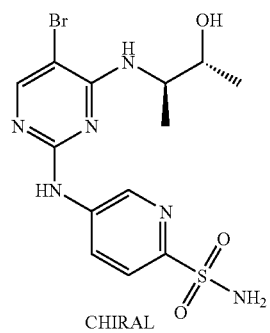

CHIRAL          CHIRAL

| Ex. No. | 3.5 | 3.6 |
|---|---|---|
| MS | EI: | EI: |
| | 419 (100%, MH+) | 419 (100%, MH+) |

|  |  |  |
|---|---|---|
| | 417 (99%) | 417 (99%) |
| | 373 (13%) | 373 (13%) |
| Angle of rotation: | Spec. angle of rotation (THF, 20° C. 589 nM): +19.0° (+0.192° at a conc. of 1.010 g/100 ml and a layer thickness of 100 mm) | Spec. angle of rotation (THF, 20° C., 589 nm): −20.0° (−0.206° at a conc. of 1.030 g/100 ml and a layer thickness of 100 mm) |
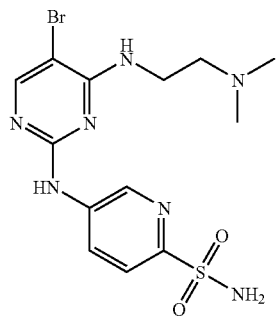 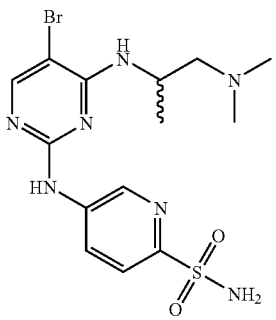
| | | |
|---|---|---|
| Ex. No. | 3.7 | 3.8 |
| MS | ESI: | ESI: |
| | 416 (42%, M+) | 430 (58%, M+) |
| | 157 (100%) | 237 (36%) |
| | 117 (83%) | 131 (100%) |
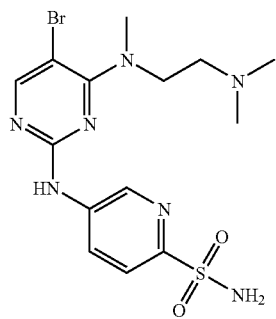 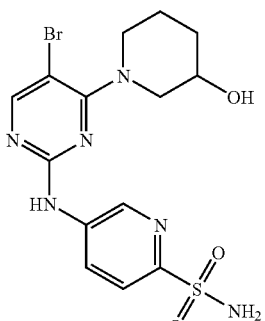
| | | |
|---|---|---|
| Ex. No. | 3.9 | 3.10 |
| MS | ESI: | ES: |
| | 430 (93%, M+) | 431 (100%, MH+) |
| | 386 (30%) | 385 (8%) |
| | 120 (100%) | |
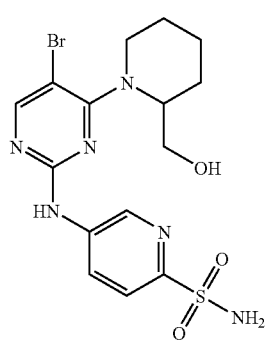 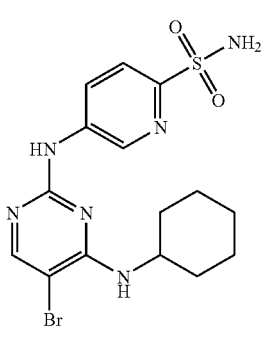
| | | |
|---|---|---|
| Ex. No. | 3.11 | 3.12 |
| MS | ES: | 426 (EI) |
| | 445 (100%, MH+) | |
| | 431 (20%) | |

-continued
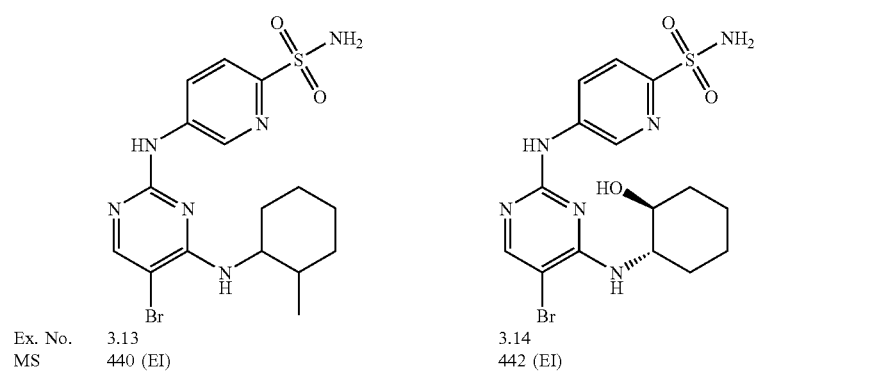
| Ex. No. | 3.13 | 3.14 |
|---|---|---|
| MS | 440 (EI) | 442 (EI) |
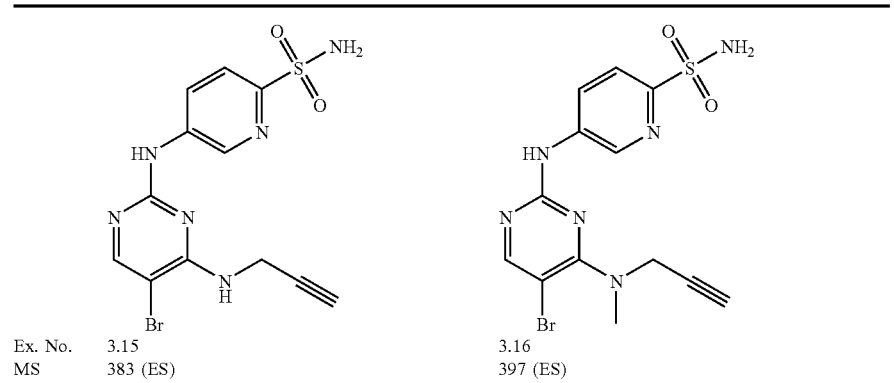
| Ex. No. | 3.15 | 3.16 |
|---|---|---|
| MS | 383 (ES) | 397 (ES) |
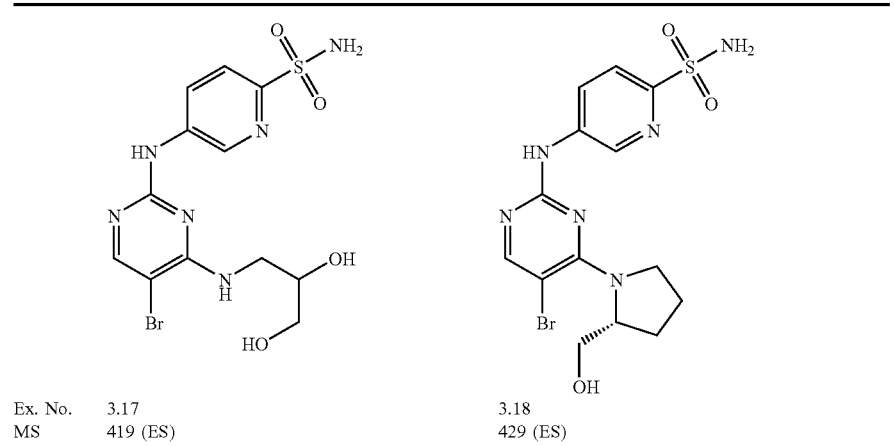
| Ex. No. | 3.17 | 3.18 |
|---|---|---|
| MS | 419 (ES) | 429 (ES) |
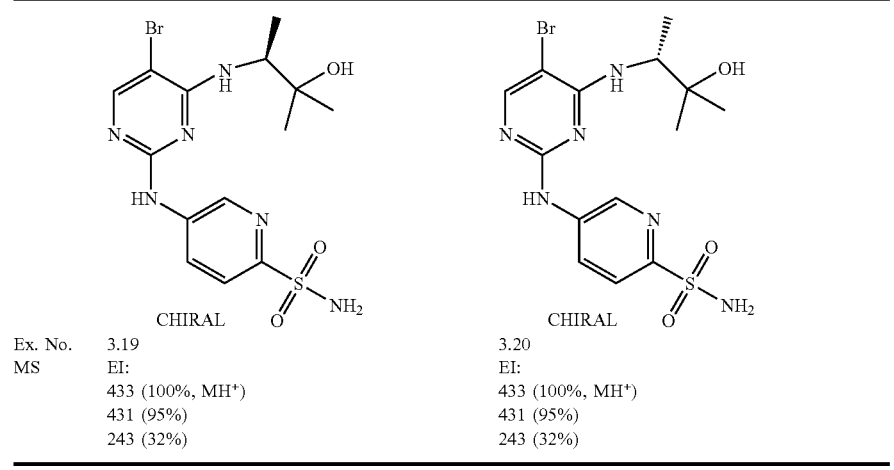
| Ex. No. | 3.19 | 3.20 |
|---|---|---|
| MS | EI: | EI: |
|  | 433 (100%, MH+) | 433 (100%, MH+) |
|  | 431 (95%) | 431 (95%) |
|  | 243 (32%) | 243 (32%) |

The enantiomer-pure amines 1,1-dimethyl-1-hydroxy-2-aminopropane (in the R- and the S-form) as starting materials for (R)-5-[5-bromo-4-(2-hydroxy-1,2-dimethyl-propylamino)-pyrimidin-2-ylamino]-pyridine-2-sulfonic acid amide (Ex. No. 3.19) and (S)-5-[5-bromo-4-(2-hydroxy-1,2-dimethyl-propylamino)-pyrimidin-2-ylamino]-pyridine-2-sulfonic acid amide (Ex. No. 3.20) were produced according to methods that are known in the literature (J. Chem. Soc. 1935; 410-416).

In addition, the compounds below were produced in a way similar to Diagram 3 and the corresponding examples.

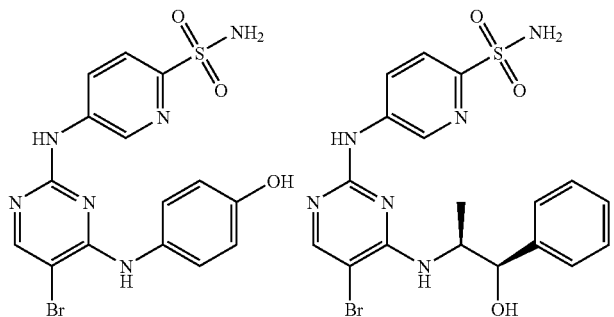

| Ex. No. | 3.21 | 3.22 |
|---|---|---|
| MS | 437 (ES) | 497 (ES) |

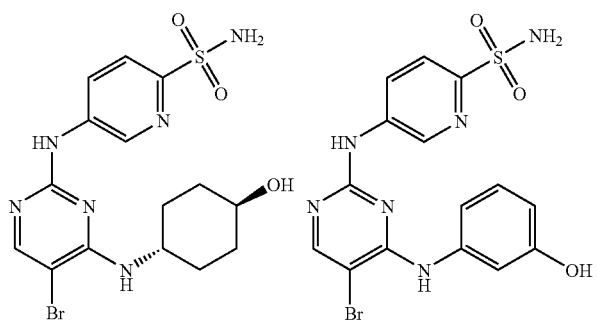

| Ex. No. | 3.23 | 3.24 |
|---|---|---|
| MS | 443 (ES) | 437 (ES) |

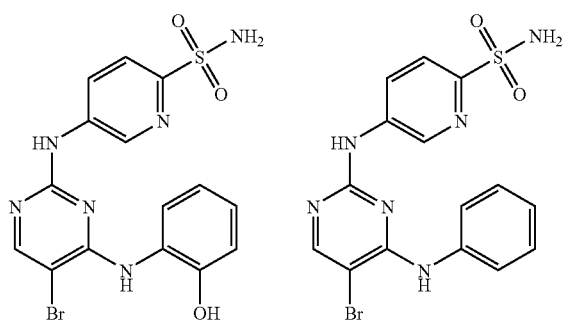

| Ex. No. | 3.25 | 3.26 |
|---|---|---|
| MS | 437 (ES) | 421 (ES) |

-continued
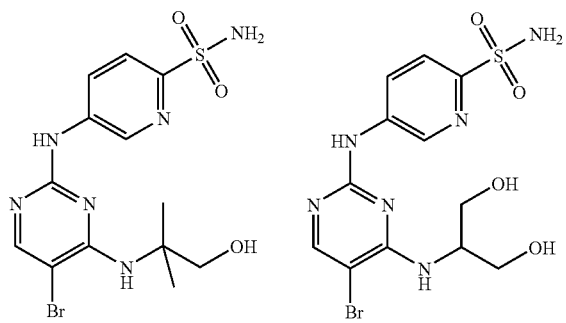
| Ex. No. | 3.27 | 3.28 |
|---|---|---|
| MS | 417 (ES) | 419 (ES) |
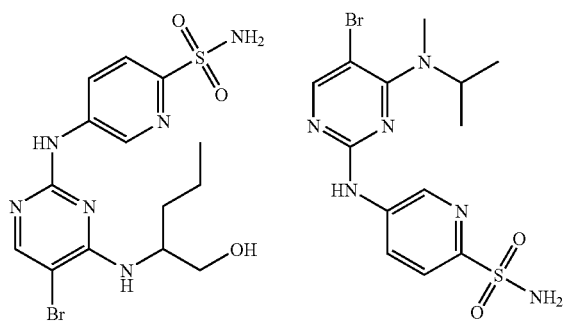
| Ex. No. | 3.29 | 3.30 |
|---|---|---|
| MS | 431 (ES) | 401 (ES) |
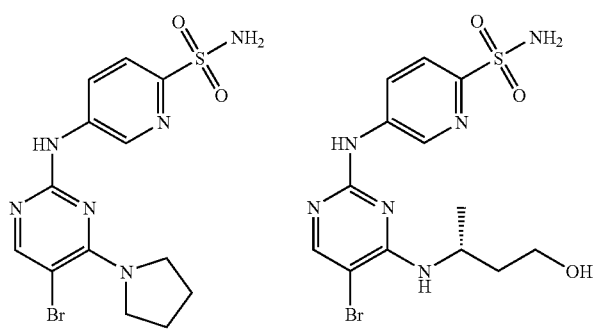
| Ex. No. | 3.31 | 3.32 |
|---|---|---|
| MS | 399 (ES) | 417 (ES) |
Diagram 4:
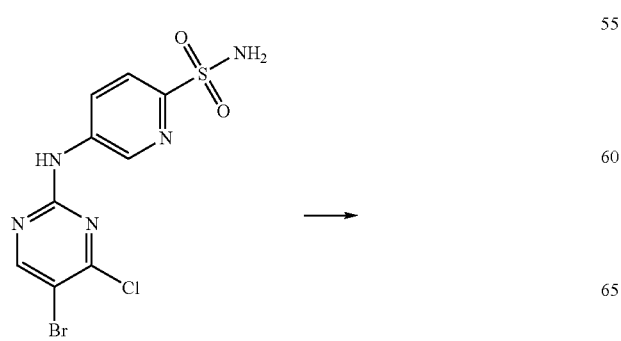

-continued

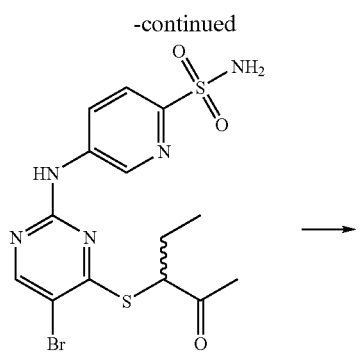

EXAMPLE 4.0

Production of 5-[5-bromo-4-(1-ethyl-2-oxo-propyl-sulfanyl)-pyrimidin-2-ylamino]-pyridine-2-sulfonic acid amide 73 mg (0.2 mmol) of 5-(5-bromo-4-chloro-pyrimidin-2-ylamino)-pyridine-2-sulfonic acid amide and 32 mg (0.27 mmol) of 3-mercapto-2-pentanone are dissolved in 4 ml of DMF p.a. After 0.038 ml (0.27 mmol) of triethylamine is added, it is allowed to stir for 2 hours at room temperature and for 3 hours at 50° C. After concentration by evaporation, it is flashed with dichloromethane/MeOH (9:1).

Yield: 37 mg (42% of theory) of 5-[5-bromo-4-(1-ethyl-2-oxo-propylsulfanyl)-pyrimidin-2-ylamino]-pyridine-2-sulfonic acid amide.

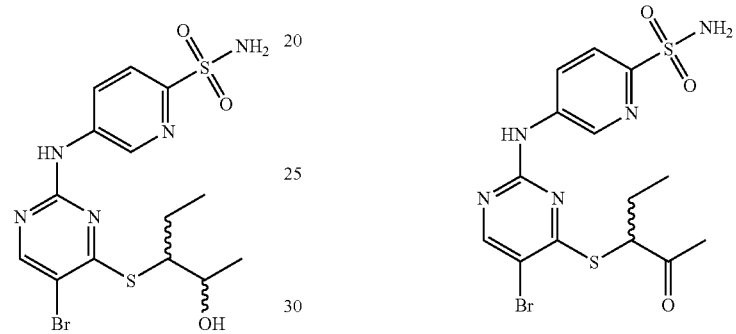

MS (ESI): 446 (91%, M+), 402 (36%), 115 (52%)

The compounds below are produced according to at least one process step of Diagram 4.

The following compounds are produced analogously according to Diagram 4 and corresponding Example 4.0:

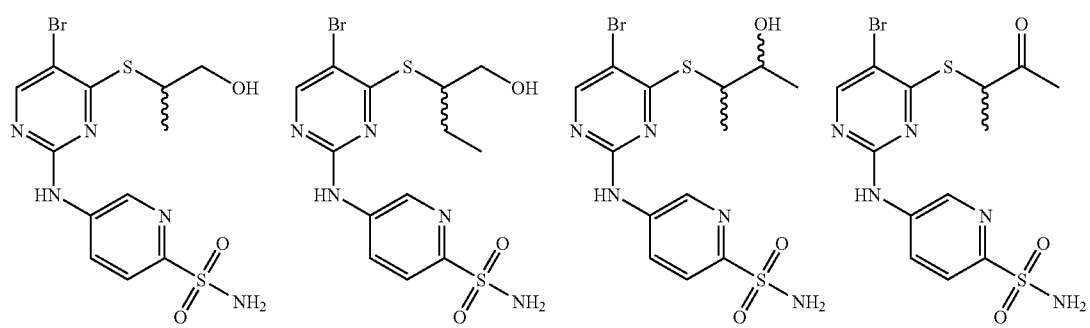

| Ex. No. | 4.1 | 4.2 | 4.3 | 4.4 |
|---|---|---|---|---|
| MS | EI: | EI: | EI: | EI: |
|  | 422 (49%, MH+) | 436 (98%, MH+) | 436 (53%, MH+) | 434 (100%, MH+) |
|  | 420 (47%) | 434 (94%) | 434 (48%) | 432 (96%) |
|  | 102 (100%) 120 (75%) | 193 (100%) | 115 (16%) |  |

EXAMPLE 4.6

Production of 5-[5-bromo-4-(1-ethyl-2-hydroxy-propylsulfanyl)-pyrimidin-2-ylamino]-pyridine-2-sulfonic acid amide 26 mg (0.058 mmol) of 5-[5-bromo-4-(1-ethyl-2-oxo-propylsulfanyl)-pyrimidin-2-ylamino]-pyridine-2-sulfonic acid amide, dissolved in 1.5 ml of THF/MeOH 1:1, is mixed with 10 mg of sodium borohydride and stirred for 3 hours at room temperature. While being cooled, 2-3 drops of glacial acetic acid are added and concentrated by evaporation. Uptake in acetonitrile and suctioning-off yield 17 mg (65% of theory) of 5-[5-bromo-4-(1-ethyl-2-hydroxy-propylsulfanyl)-pyrimidin-2-ylamino]-pyridine-2-sulfonic acid amide.

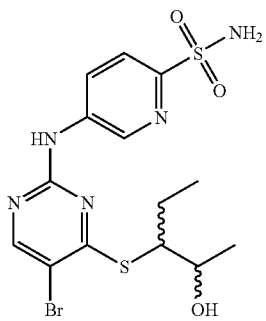

MS (ESI): 448 (45%, M+), 404 (13%), 142 (47%)

Diagram 5:

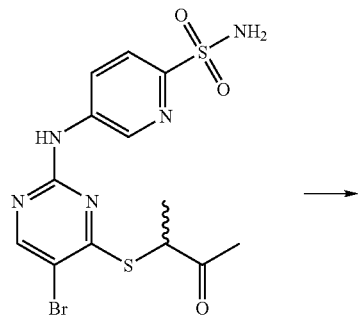

EXAMPLE 5.0

Production of 5-[5-bromo-4-(2-hydroxy-1,2-dimethyl-propylsulfanyl)-pyrimidin-2-ylamino]-pyridine-2-sulfonic acid amide 108 mg (0.25 mmol) of 5-[5-bromo-4-(1-methyl-2-oxo-propylsulfanyl)-pyrimidin-2-ylamino]-pyridine-2-sulfonic acid amide is dissolved in tetrahydrofuran p.a. at 4° C. that is mixed in portions with 1 ml (3 mmol) of methylmagnesium bromide (3 M in ether). After 24 hours of stirring at room temperature, it is quenched by adding ammonium chloride solution. After extraction with ethyl acetate, the dried residue is flashed with dichloromethane/methanol.

Yield: 75 mg (67% of theory) of 5-[5-bromo-4-(2-hydroxy-1,2-dimethyl-propylsulfanyl)-pyrimidin-2-ylamino]-pyridine-2-sulfonic acid amide.

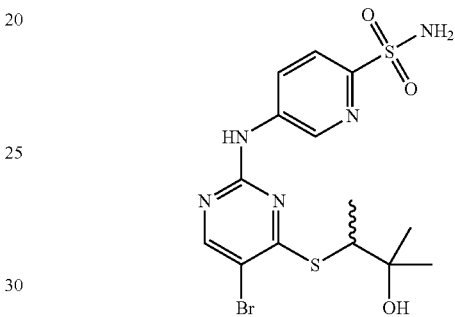

MS (EI): 450 (100%, MH+), 432(100%), 430 (90%)

Diagram 6:

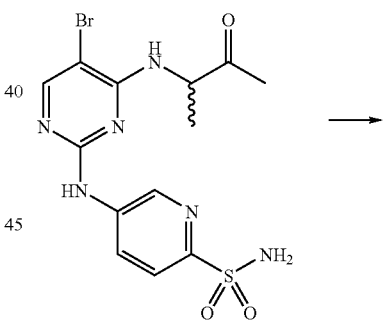

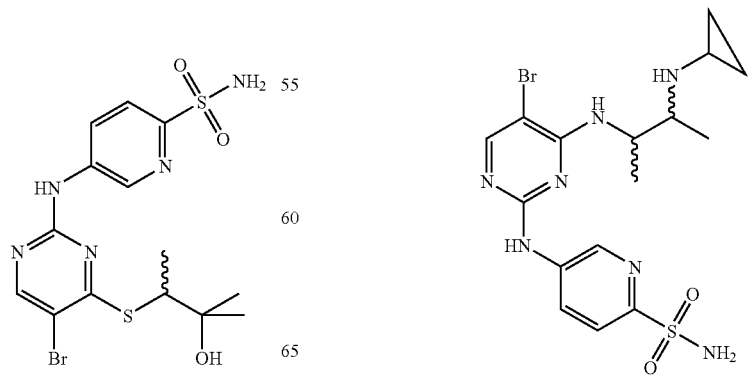

EXAMPLE 6.0

Production of 5-[5-bromo-4-(2-cyclopropylamino-1-methyl-propylamino)-pyrimidin-2-ylamino]-pyridine-2-sulfonic acid amide 62.5 mg (0.15 mmol) of 5-[5-bromo-4-(1-methyl-2-oxo-propylamino)-pyrimidin-2-ylamino]-pyridine-2-sulfonic acid amide is mixed in 4 ml of 1,2-dichloroethane with 50 mg of cyclopropylamine.

After 15 minutes, 20 mg of sodium cyanoborohydride is added, and it is stirred for 24 hours. The reaction mixture is concentrated by evaporation and flashed with dichloromethane/methanol.

Yield: 21 mg (31% of theory) of 5-[5-bromo-4-(2-cyclopropylamino-1-methyl-propylamino)-pyrimidin-2-ylamino]-pyridine-2-sulfonic acid amide.

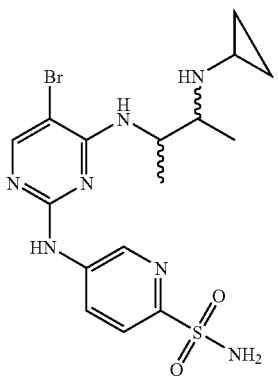

NMR (d$_6$-DMSO): 9.86 (1H, s), 8.95 (1H, d), 8.36 (1H, dd), 8.13 (1H, s), 7.81 (1H, dd), 7.25 (2H, s), 6.51 (1H, d), 4.03 (1H, m), 2.90 (1H, m), 2.20 (1H, m), 1.25 (3H, d), 1.10 (3H, d), 0.1-0.5 (4H, m)

Diagram 7:

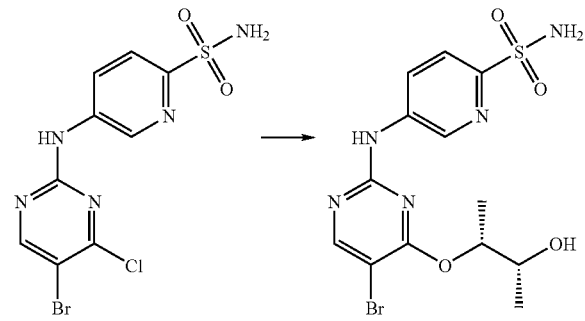

EXAMPLE 7.0

Production of 5-[5-bromo-4-(2-hydroxy-1-methyl-propoxy)-pyrimidin-2-ylamino]-pyridine-2-sulfonic acid amide 270 mg (1.5 mmol) of (2R, 3R)-(−)-2,3-butanediol is dissolved in 3 ml of pyridine and mixed with 30 mg (0.69 mmol) of sodium hydride. It is allowed to stir for 15 minutes at room temperature and then 110 mg (0.3 mmol) of 5-(5-bromo-4-chloro-pyrimidin-2-ylamino)-pyridine-2-sulfonic acid amide is added. After 1 hour at room temperature, it is stirred for 4 more hours at 50° C. Concentration by evaporation and flashing with dichloromethane/MeOH 4:1 yields 42 mg of 5-[5-bromo-4-(2-hydroxy-1-methyl-propoxy)-pyrimidin-2-ylamino]-pyridine-2-sulfonic acid amide: (34% of theory)°

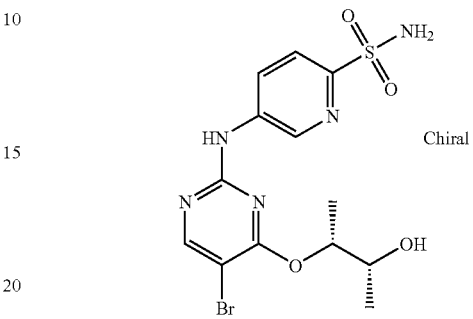

$^1$H-NMR (DMSO): 10.3 (s, 1H), 8.95 (d, 1H), 8.5 (s, 1H), 8.36 (dd, 1H), 7.88 (d, 1H), 7.32 (s, 2H), 5.2 (m, 1H), 4.92 (d, 1H), 3.85 (m, 1H), 1.3 (d, 3H), 1.1 (d, 3H)

Production of the Intermediate Stages Preferably Used for the Synthesis of the Compounds of General Formula I or I$_f$ According to the Invention The examples below describe the production of the intermediate products that are preferably used for the synthesis of the compounds of general formula I according to the invention.

EXAMPLE a)

(R)-2-(5-Bromo-2-chloro-pyrimidin-4-ylamine)-3-methyl-butan-1-ol

A solution of 9.129 g (40 mmol) of 5-bromo-2,4-dichloro-pyrimidine in 40 ml of acetonitrile is mixed at 0° C. with 7.0 ml (48 mmol) of triethylamine and 4.902 g (48 mmol) of (R)-(−)-2-amino-3-methylbutanol. The reaction mixture is heated slowly to room temperature by removal of the ice bath, and it is further stirred overnight. The precipitate that is formed is suctioned off, washed with water and dried.

9.133 g (31 mmol, 78% of theory) of the product is obtained as a white solid.

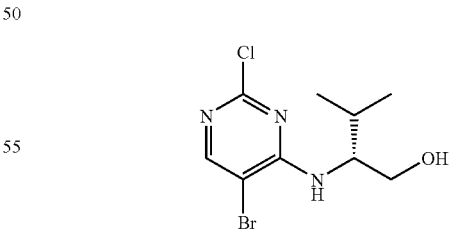

$^1$H-NMR: 8.25 (s, 1H), 6.78 (br, 1H), 4.67 (br, 1H), 3.98 (m, 1H), 3.59 (m, 2H), 1.98 (m, 1H), 0.94 (d, 3H), 0.86 (d, 3H).

$^{13}$C-NMR: 159.8s, 158.2s, 156.8d, 102.7s, 60.7t, 58.3d, 28.9d, 19.5q, 19.0q.

MS: 295 (EI)

Solvent: DMSO

EXAMPLE b)

4-(5-Bromo-2-chloro-pyrimidin-4-ylsulfanyl)-butan-1-ol

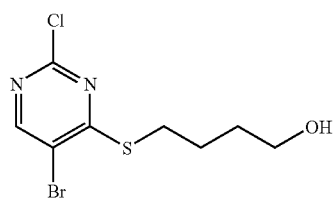

A solution of 2.27 g (10.0 mmol) of 5-bromo-2,4-dichloro-pyrimidine in 30 ml of acetonitrile is mixed while being stirred at −20° C. with 1.39 ml (10 mmol) of triethylamine. Then, a solution of 1.06 g (10 mmol) of 4-mercapto-1-butanol in 1 ml of acetonitrile is added in drops. The reaction mixture is heated overnight to room temperature while being stirred. The batch is filtered, and the filtrate is evaporated to the dry state. The residue that is obtained is purified by chromatography (Flashmaster II, hexane/ethyl acetate 1:1). 2.89 g (9.7 mmol, 97% of theory) of the product 4-(5-bromo-2-chloro-pyrimidin-4-ylsulfanyl)-butan-1-ol is obtained.

$^1$H-NMR: 8.65 (s, 1H), 4.45 (t, 1H), 3.45 (m, 2H), 3.19 (m, 2H), 1.73 (m, 2H), 1.55 (M, 2H).

MS: 297 (CI)

The following intermediate products are produced in a way similar to Examples a) and b).

EXAMPLE n)

a) (R)-4-[5-Bromo-4(2-hydroxy-1-methyl-ethylamino)-pyrimidin-2-y.amino]-thiophene-2-sulfonyl fluoride

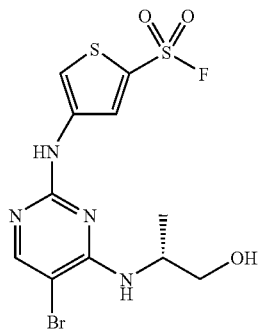

324 mg (1.2 mmol) of (R)-2-(5-bromo-2-chloro-pyrimidin-4-ylamino)-propan-1-ol is added to a suspension of 330 mg of a mixture that consists of 4-amino-thiophene-2-sulfonyl fluoride and 5-amino-thiophene-2-sulfonyl fluoride (ratio: 3:1) in 5 ml of acetonitrile, 0.5 ml of water and 0.5 ml of a 4 molar solution of hydrochloric acid in 1,4-dioxane. The reaction mixture is stirred under reflux for 26 hours. After cooling, the batch is concentrated by evaporation, and the residue is stirred with ethanol. The precipitate that is formed is suctioned off and stirred with warm water. In turn,

| Example | c | d | e | f |
|---|---|---|---|---|
| | 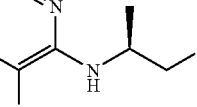 | 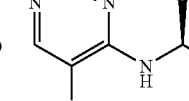 | 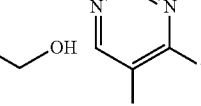 | 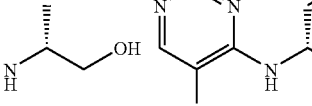 |
| MS | 280 (CI) | 295 (EI) | 265 (EI) | 279 (EI) |

| Example | g | h | i | j |
|---|---|---|---|---|
| |  | 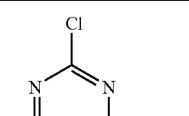 | 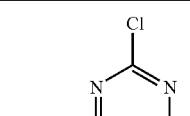 | 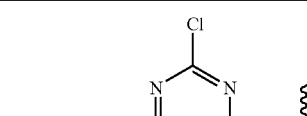 |
| MS | 279 (EI) | 201 (EI) | 261 (EI) | 325 (CI) |

| Example | k | l | m |
|---|---|---|---|
| | 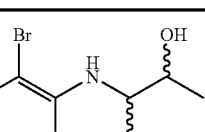 | 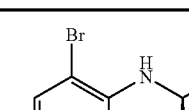 | 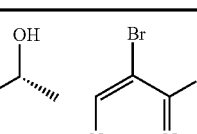 |
| MS | 281 (EI) | 281 (EI) | 279 (EI) | the solid is suctioned off and dried. 152 mg (0.37 mmol, 31% of theory) of the product 4-[5-bromo-4-(2-hydroxy-1-methyl-ethylamino)-pyrimidin-2-ylamino]-thiophene-2-sulfonyl fluoride is obtained.

$^1$H-NMR: 10.59 (s, 1H), 8.28 (s, 1H), 8.18 (m, 2H), 7.22 (br, 1H), 4.18 (m, 1H), 3.50 (m, 2H), 1.18 (d, 3H).

MS: 411 (ES).

EXAMPLE o)

4-Amino-thiophene-2-sulfonic acid amide (A) and 5-amino-thiophene-2-sulfonic acid amide (B)

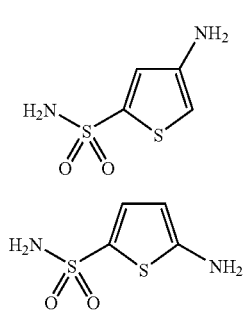

A solution of 11.3 g (49.6 mmol) of a mixture that consists of 4-nitro-thiophene-2-sulfonyl chloride and 5-nitro-thiophene-2-sulfonyl chloride (ratio: 1.4/1.0) in acetone is added while being stirred to a saturated solution of ammonia in 170 ml of acetone at −35° C. After 30 minutes, the batch is filtered and concentrated by evaporation. The crude product is dissolved without further purification in 100 ml of ethanol. It is mixed with 6 g of Raney nickel and hydrogenated for 8 hours under low pressure at room temperature. The batch is filtered and concentrated by evaporation. 11.7 g of a mixture that consists of 4-amino-thiophene-2-sulfonic acid amide and 5-amino-thiophene-2-sulfonic acid amide is obtained at a ratio of 2:1, which is used without further purification.

$^1$H-NMR (DMSO): 7.48 (s, 2H, A), 7.13 (s, 2H, B), 7.03 (m, 2H, A+B), 6.33 (s, 2H, B), 6.20 (d, 1H, A), 5.78 (d, 1H, B), 5.07 (s, 2H, A).

MS: 179 (ES).

EXAMPLE o'

4-Amino-thiophene-2-sulfonic acid amide

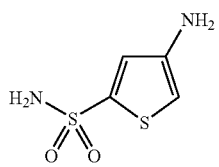

15 g of a crude mixture that consists of 4-amino-thiophene-2-sulfonic acid amide and 5-amino-thiophene-2-sulfonic acid amide in a ratio of about 2:1 is purified by chromatography (DCM/EtOH 9:1) on silica gel. 2.7 g of the product 4-amino-thiophene-2-sulfonic acid amide is obtained.

$^1$H-NMR (DMSO): 7.48 (s, 2H), 7.02 (d, 1H), 6.20 (d, 1H), 5.07 (s, 2H).

MS: 179 (ES).

EXAMPLE p)

4-Nitro-thiophene-2-sulfonyl chloride (A) and 5-Nitro-thiophene-2-sulfonyl chloride (B)

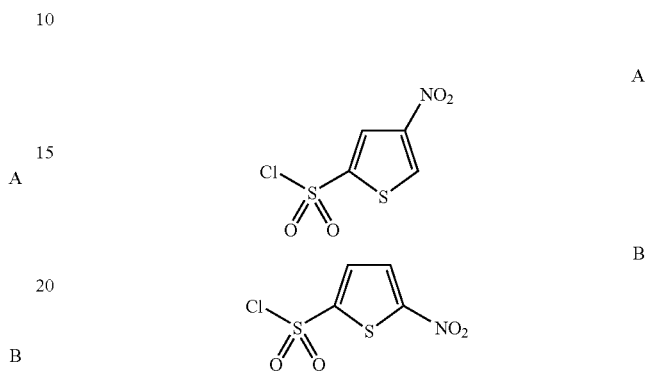

A solution of 25 g (137 mmol) of thiophene-2-sulfonyl chloride in 20 ml of dichloromethane is slowly added in drops to 98 ml of concentrated nitric acid while being stirred. The reaction mixture is stirred for 2 hours at 40° C. and then added to ice. It is extracted with dichloromethane (2×). The combined organic phases are dried on MgSO$_4$, filtered and concentrated by evaporation. 24 g (105 mmol, corresponding to 77% of theory) of a mixture of the products 4-nitro-thiophene-2-sulfonyl chloride and 5-nitro-thiophene-2-sulfonyl chloride in a ratio of 1.4/1.0 is obtained.

$^1$H-NMR (DMSO): 8.63 (d, 1H, A), 7.93 (d, 1H, B), 7.54 (d, 1H, A), 7.18 (d, 1H, B)

EXAMPLE q)

4-Amino-thiophene-2-sulfonyl fluoride (A) and 5-amino-thiophene-2-sulfonyl fluoride (B)

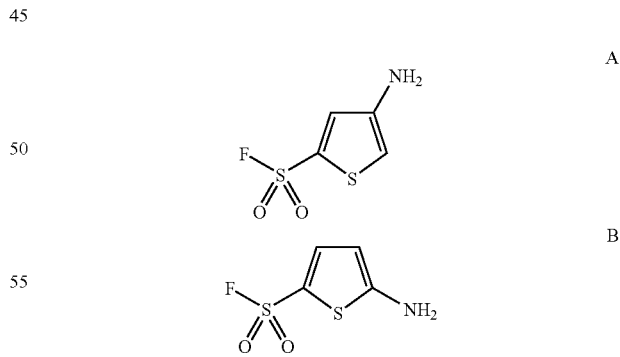

1.57 g (7.4 mmol) of a mixture that consists of 4-nitro-thiophene-2-sulfonyl fluoride and 5-nitro-thiophene-2-sulfonyl fluoride in a ratio of 1.4/1.0 is dissolved in 20 ml of ethanol, mixed with 1.57 g of Raney nickel and then hydrogenated under low pressure for 4 hours at 40° C. The hydrogen pressure is increased to 10 bar and hydrogenated for another 5 hours at 50° C. The batch is filtered and concentrated by evaporation. The crude product is purified by chromatography (ethyl acetate/hexane 4:1). 381 mg (2.1 mmol, 28% of theory) of a mixture that consists of 4-amino-thiophene-2-sulfonyl fluoride (A) and 5-amino-thiophene-2-sulfonyl fluoride (B) in a ratio of 3/1 is obtained.

$^1$H-NMR (DMSO): 7.68 (d, 1H, B), 7.62 (s, 2H, B), 7.51 (d, 1H, A), 6.83 (d, 1H, A), 6.07 (d, 1H, B), 5.45 (s, 2H, A).

$^{19}$F-NMR (DMSO): 181.3 (A), 180.6 (B).

MS: 181 (CI)

EXAMPLE r)

4-Nitro-thiophene-2-sulfonyl fluoride (A) and 5-nitro-thiophene-2-sulfonyl fluoride (B)

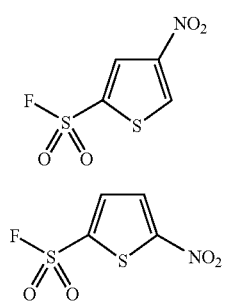

9.47 g (41.6 mmol) of a mixture that consists of 4-nitro-thiophene-2-sulfonyl chloride and 5-nitro-thiophene-2-sulfonyl chloride in a ratio of 1.4/1.0 is mixed with a solution of 4.83 g (83.2 mmol) of potassium fluoride in 12 ml of water and stirred under reflux for 90 minutes. After cooling, the batch is added to ice water and extracted using ethyl acetate. The combined organic phases are dried, filtered and concentrated by evaporation. 5.4 g (25.6 mmol, corresponding to 61% of theory) of a mixture of the products 4-nitro-thiophene-2-sulfonyl fluoride (A) and 5-nitro-thiophene-2-sulfonyl fluoride (B) in a ratio of 1.4/1.0 is obtained.

$^1$H-NMR (DMSO): 9.35 (d, 1H, A), 8.79 (d, 1H, B), 8.34 (m, 2H, A+B).

$^{19}$F-NMR (DMSO): 181.3 (A), 180.6 (B).

Subjects of this invention are thus also compounds of general formula Ia

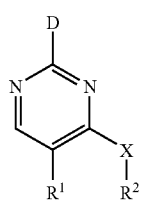

in which

D stands for halogen, and X, R$^1$ and R$^2$ have the meanings that are indicated in general formula (I) or (I$_f$) and their use as intermediate products for the production of compounds of general formula (I).

Those intermediate products of general formula Ia, in which D stands for chlorine and X, R$^1$ and R$^2$ have the meanings that are indicated in general formula (I) or of) are especially valuable.

Those intermediate products of general formula Ia, in which D stands for chlorine, X stands for sulfur or the group —NH—, R$^1$ stands for bromine or chlorine and R$^2$ has the meaning that is indicated in general formula (I) or (I$_f$) are quite especially valuable.

Compounds of general formula Ib (Ib)

in which

R$^1$ and R$^2$ have the meanings that are indicated in general formula (I) or (I$_f$) and their use as intermediate products for the production of the compound of general formula I, represent another subject of this invention.

Those compounds of general formula Ib, in which R$^1$ stands for halogen and R$^2$ has the meaning that is indicated in general formula (I) or (I$_f$), are especially valuable.

Another subject of the invention relates to compounds of general formula Ic (Ic)

in which

X stands for halogen or NH$_2$ and

Y stands for hydrogen, and Z stands for NH$_2$ or NO$_2$ or

Y stands for NH$_2$ or NO$_2$ and Z stands for hydrogen, as well as their use as intermediate products for the production of the compound of general formula (I) or (I$_f$).

The agents according to the invention can also be used for treating cancer, auto-immune diseases, cardiovascular diseases, chemotherapy agent-induced alopecia and mucositis, infectious diseases, nephrological diseases, chronic and acute neurodegenerative diseases and viral infections, whereby cancer is defined as solid tumors and leukemia; auto-immune diseases are defined as psoriasis, alopecia and multiple sclerosis; cardiovascular diseases are defined as stenoses, arterioscleroses and restenoses; infectious diseases are defined as diseases that are caused by unicellular parasites; nephrological diseases are defined as glomerulonephritis; chronic neurodegenerative diseases are defined as Huntington's disease, amyotrophic lateral sclerosis, Parkinson's disease, AIDS, dementia and Alzheimer's disease; acute neurodegenerative diseases are defined as ischemias of the brain and neurotraumas; and viral infections are defined as cytomegalic infections, herpes, hepatitis B or C, and HIV diseases.

The following examples describe the biological action of the compounds according to the invention without limiting the invention to these examples.

SAMPLE APPLICATION 1

CDK2/CycE Kinase Assay

Recombinant CDK2- and CycE-GST-fusion proteins, purified from baculovirus-infected insect cells (Sf9), were purchased by the Proquinase Company, Freiburg. Histone IIIS, which was used as a kinase substrate, was purchased by the Sigma Company.

CDK2/CycE (50 ng/measuring point) was incubated for 15 minutes at 22° C. in the presence of various concentrations of test substances (0 μm, as well as within the range of 0.01-100 μm) in assay buffer [50 mmol of tris/HCl pH 8.0, 10 mmol of $MgCl_2$, 0.1 mmol of Na ortho-vanadate, 1.0 mmol of dithiothreitol, 0.5 μm of adenosine triphosphate (ATP), 10 μg/measuring point of histone IIIS, 0.2 μCi/measuring point of $^{33}$P-gamma ATP, 0.05% NP40, 12.5% dimethyl sulfoxide]. The reaction was stopped by adding EDTA solution (250 mmol, pH 8.0, 14 μl/measuring point).

From each reaction batch, 10 μl was applied to P30 filter strips (Wallac Company), and non-incorporated $^{33}$P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated $^{33}$P (substrate phosphorylation) was determined by scintillation measurement in a gamma-radiation measuring device (Wallac).

SAMPLE APPLICATION 2

Proliferation Assay

Cultivated human tumor cells (as indicated) were flattened out at a density of 5000 cells/measuring point in a 96-well multititer plate in 200 μl of the corresponding growth medium. After 24 hours, the cells of one plate (zero-point plate) were colored with crystal violet (see below), while the medium of the other plates was replaced by fresh culture medium (200 μl), to which the test substances were added in various concentrations (0 μm, as well as in the range of 0.01-30 μm; the final concentration of the solvent dimethyl sulfoxide was 0.5%). The cells were incubated for 4 days in the presence of test substances. The cell proliferation was determined by coloring the cells with crystal violet: the cells were fixed by adding 20 μl/measuring point of a 11% glutaric aldehyde solution for 15 minutes at room temperature. After three washing cycles of the fixed cells with water, the plates were dried at room temperature. The cells were colored by adding 100 μl/measuring point of a 0.1% crystal violet solution (pH was set at 3 by adding acetic acid). After three washing cycles of the colored cells with water, the plates were dried at room temperature. The dye was dissolved by adding 100 μl/measuring point of a 10% acetic acid solution. The extinction was determined by photometry at a wavelength of 595 nm. The change of cell growth, in percent, was calculated by standardization of the measured values to the extinction values of the zero-point plate (=0%) and the extinction of the untreated (0 μm) cells (=100%).

The results of sample applications 1 and 2 are indicated in the following table.

| Number Example | Inhibition $IC_{50}$ [nM] CDK2/CycE | Proliferation $IC_{50}$ [μM] MCF7 |
|---|---|---|
| 1.7 | 6 | — |
| 1.8 | 87 | 3 |
| 1.9 | 50 | — |
| 1.11 | 40 | 1.2 |
| 1.12 | 22 | 0.24 |
| 1.13 | 8 | <0.1 |
| 1.14 | 17 | 0.87 |
| 1.15 | 13 | 2 |
| 1.16 | 36 | 2 |
| 1.17 | 7 | 0.5 |
| 1.19 | 12 | — |
| 1.20 | 13 | 1.9 |
| 1.21 | 30 | 5.3 |
| 3.3 | 36 | 0.62 |
| 3.4 | 58 | 0.84 |
| 3.5 | <10 | 0.88 |
| 3.6 | <10 | 0.1 |
| 3.12 | 20 | 0.79 |
| 3.13 | 16 | 0.3 |
| 4.1 | <10 | 0.61 |
| 4.2 | <10 | 0.26 |
| 4.3 | 34 | 0.23 |
| 4.6 | 74 | 0.63 |
| 6.0 | 25 | 2.3 |

Proof of superiority of the Compounds According to the Invention Compared to the Known Compounds To prove the superiority of the compounds according to the invention compared to the known compounds, the compounds according to the invention were compared to known reference compounds and structurally-similar known compounds in the enzyme test. The result is cited in the following table:

| Example No. | CDK2/CycE IC$_{50}$ [nM] | MCF-7 IC$_{50}$ [μM] |
|---|---|---|
| 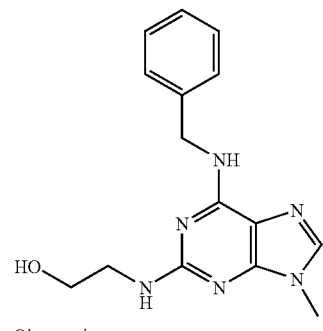  Olomoucine | 7000 | 30 |
| Chiral 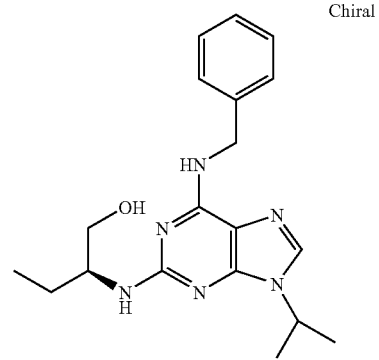  Roscovitine | 1500 | 8 |
| 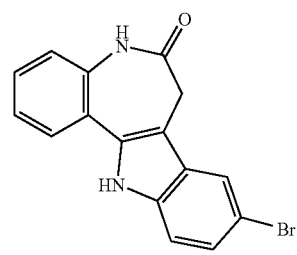  Kenpaullone | 1800 | 6 |
| 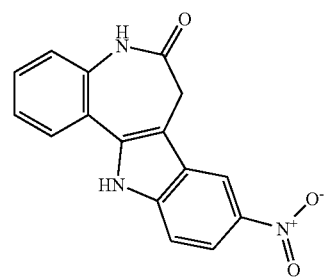  Alsterpaullone | 90 | 1.2 |

| Example No. | CDK2/CycE IC$_{50}$ [nM] | MCF-7 IC$_{50}$ [µM] |
|---|---|---|
| 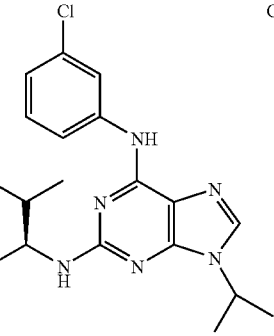 Purvalanol A | 10 | 2 |
| Example 11 from WO01/14375 (page 38)  | 190 | |

It can be seen from the table that both in the enzyme test and in the cell test, the compounds according to the invention have significantly higher activities in the enzyme and in the MCF-7 cells than the compounds that are known from the prior art. The compounds according to the invention are thus far superior to the known compounds.

The entire disclosures of all applications, patents and publications, cited herein and of corresponding German Patent Application No. 102 55 948.8, filed Nov. 26, 2002 and German Patent Application No. 102 12 100.1, filed Mar. 11, 2002, and U.S. Provisional Application Ser. No. 60/363,878, filed Mar. 14, 2002 and U.S. Provisional Application No. 60/430,053, filed Dec. 2, 2002, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

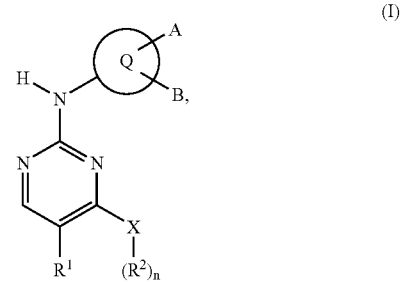

wherein

Q stands for pyridine, thiophene, 1,3,4-thiadiazole, or 1,2,4-triazole, $R^1$ stands for bromine or chlorine, $R^2$ stands for $C_2$-$C_{10}$-alkinyl or for $C_1$-$C_{10}$-alkyl, phenyl or $C_3$-$C_7$-cycloalkyl that is optionally substituted in one or more places in the same way or differently with hydroxy, $C_1$-$C_6$-alkyl, $C_1$-$C_6$-alkoxy, $COR^5$, $C_3$-$C_7$-cycloalkyl, —N($C_1$-$C_6$-alkyl)$_2$, —NH$C_3$-$C_7$-cycloalkyl or phenyl, wherein the $C_3$-$C_7$-cycloalkyl ring optionally can be interrupted by one or more nitrogen, oxygen and/or sulfur atoms and/or can be interrupted by one or more =C=O groups in the ring and/or optionally one or more possible double bonds can be contained in the ring, and wherein phenyl or $C_3$-$C_7$-cycloalkyl is optionally substituted with hydroxy, X stands for oxygen, sulfur or for the group —NH— or for —N($C_1$-$C_3$-alkyl)-, or X and $R^2$ together form a piperidine or a pyrrolidine ring, which optionally can be substituted in one or more places with hydroxy, $C_1$-$C_6$-alkyl, hydroxy-$C_1$-$C_6$-alkyl or halogen, A and B are, in each case independently of one another, hydrogen, chlorine or the group —$SR^7$, —$S(O)R^7$ or —$SO_2R^7$, $R^3$ and $R^4$ are, in each case independently of one another, hydrogen or $C_1$-$C_6$-alkyl that is optionally substituted in one or more places in the same way or differently with hydroxy, $C_1$-$C_6$-alkoxy, $C_1$-$C_6$-alkylthio, —N($C_1$-$C_6$-alkyl)$_2$, the group $R^6$ or —N($C_1$-$C_6$-alkyl)-$R^6$, $R^5$ stands for $C_1$-$C_6$-alkyl, $R^6$ stands for $C_3$-$C_7$-cycloalkyl that is optionally substituted in one or more places in the same way or differently with halogen, hydroxy, $C_1$-$C_6$-alkyl, $C_1$-$C_6$-alkoxy or —$SO_2NR^3R^4$, wherein the $C_3$-$C_7$-cycloalkyl ring optionally can be interrupted by one or more nitrogen, oxygen and/or sulfur atoms and/or can be interrupted by one or more =C=O groups in the ring and/or optionally one or more possible double bonds can be contained in the ring, benzylthio, furan, imidazole, morpholine, oxolane, phenyl, phenyloxy, piperidine, pyridine, pyrazine, pyrrolidine or y-butyrolactam ring, $R^7$ stands for $C_1$-$C_6$-alkyl, benzyl or for the group —$NR^3R^4$, and n stands for 1, or a salt thereof.

2. A compound according to claim 1, wherein $R^2$ stands for $C_2$-$C_{10}$-alkinyl or for $C_1$-$C_{10}$-alkyl, phenyl or $C_3$-$C_7$-cycloalkyl that is optionally substituted in one or more places in the same way or differently with hydroxy, $C_1$-$C_6$-alkyl, $C_1$-$C_6$-alkoxy, $COR^5$, $C_3$-$C_7$-cycloalkyl, —N($C_1$-$C_6$-alkyl)$_2$, —NH$C_3$-$C_7$-cycloalkyl or phenyl, and wherein phenyl or $C_3$-$C_7$-cycloalkyl is optionally substituted with hydroxy, and $R^6$ stands for $C_3$-$C_7$-cycloalkyl that is optionally substituted in one or more places in the same way or differently with halogen, hydroxy, $C_1$-$C_6$-alkyl, $C_1$-$C_6$-alkoxy or —$SO_2NR^3R^4$, benzylthio, furan, imidazole, morpholine, oxolane, phenyl, phenyloxy, piperidine, pyridine, pyrazine, pyrrolidine or y-butyrolactam ring, $R^7$ stands for $C_1$-$C_6$-alkyl, benzyl or for the group —$NR^3R^4$.

3. A compound according to claim 1, wherein Q stands for pyridine.

4. A compound according to claim 1, wherein Q stands for thiophene.

5. A compound according to claim 1, wherein Q stands for 1,3,4-thiadiazole.

6. A compound according to claim 1, wherein Q stands for 1,2,4-triazole.

7. A compound according to claim 1, wherein $R^2$ stands for $C_2$-$C_{10}$-alkinyl or for $C_1$-$C_{10}$-alkyl.

8. A compound according to claim 1, wherein $R^2$ stands for $C_3$-$C_7$-cycloalkyl.

9. A compound according to claim 1, wherein $R^1$ stands for bromine.

10. A compound according to claim 1, wherein $R^1$ stands for chlorine.

11. A compound according to claim 1, wherein X stands for oxygen.

12. A compound according to claim 1, wherein X stands for sulfur.

13. A compound according to claim 1, wherein X stands for the group —NH— or for —N($C_1$-$C_3$-alkyl)-.

14. A compound according to claim 1, wherein X and $R^2$ together form a piperidine or a pyrrolidine ring.

15. A compound according to claim 1, wherein at least one of A and B is —$SR^7$, —$S(O)R^7$ or —$SO_2R^7$.

16. A compound according to claim 1, wherein at least one of A and B is chlorine.

17. A pharmaceutical composition comprising a compound according to claim 1 and a pharmaceutically acceptable carrier.

18. A pharmaceutical composition comprising a compound according to claim 2 and a pharmaceutically acceptable carrier.

19. A method for treating breast cancer comprising administering to a patient in need thereof an effective amount of a compound according to claim 1.

20. A method for treating breast cancer comprising administering to a patient in need thereof an effective amount of a compound according to claim 2.

21. A method according to claim 19, wherein a cyclin-dependent kinase is inhibited in the treatment of breast cancer.

22. A method according to claim 21, wherein the kinase inhibited in the treatment of breast cancer is CDK1, CDK2, CDK3, CDK4, CDK5, CDK6, CDK7, CDK8 or CDK9.

23. A method according to claim 19, wherein a glycogen-synthase-kinase (GSK-3β) is inhibited in the treatment of breast cancer.

24. A method according to claim 19, wherein the administration is enteral, parenteral or oral administration.

* * * * *

UNITED STATES PATENT AND TRADEMARK OFFICE
CERTIFICATE OF CORRECTION

| | |
|---|---|
| PATENT NO. | : 7,288,547 B2 |
| APPLICATION NO. | : 10/384787 |
| DATED | : October 30, 2007 |
| INVENTOR(S) | : Ulrich Luecking |

It is certified that error appears in the above-identified patent and that said Letters Patent is hereby corrected as shown below:

On Title Page, Item [22] Filing Date Reads "Oct. 27, 2003" should read -- March 11, 2003 --

Signed and Sealed this

Thirteenth Day of May, 2008

JON W. DUDAS
*Director of the United States Patent and Trademark Office*